(12) United States Patent
Conway et al.

(10) Patent No.: US 9,833,479 B2
(45) Date of Patent: *Dec. 5, 2017

(54) GENE CORRECTION OF SCID-RELATED GENES IN HEMATOPOIETIC STEM AND PROGENITOR CELLS

(71) Applicant: Sangamo Therapeutics, Inc., Richmond, CA (US)

(72) Inventors: Anthony Conway, Richmond, CA (US); Gregory J. Cost, Richmond, CA (US); Michael C. Holmes, Richmond, CA (US); Fyodor Urnov, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/458,258

(22) Filed: Mar. 14, 2017

(65) Prior Publication Data

US 2017/0189450 A1 Jul. 6, 2017

Related U.S. Application Data

(63) Continuation of application No. 14/813,924, filed on Jul. 30, 2015, now Pat. No. 9,616,090.

(60) Provisional application No. 62/030,942, filed on Jul. 30, 2014.

(51) Int. Cl.

| | |
|---|---|
| *A61K 35/28* | (2015.01) |
| *C12N 9/22* | (2006.01) |
| *C12N 15/90* | (2006.01) |
| *A61K 38/17* | (2006.01) |
| *C07K 14/715* | (2006.01) |
| *C07K 14/47* | (2006.01) |
| *A61K 35/12* | (2015.01) |

(52) U.S. Cl.
CPC .......... *A61K 35/28* (2013.01); *A61K 38/1709* (2013.01); *A61K 38/1793* (2013.01); *C07K 14/4705* (2013.01); *C07K 14/7155* (2013.01); *C12N 9/22* (2013.01); *C12N 15/907* (2013.01); *A61K 2035/124* (2013.01)

(58) Field of Classification Search
None
See application file for complete search history.

(56) References Cited

U.S. PATENT DOCUMENTS

| | | |
|---|---|---|
| 5,420,032 A | 5/1995 | Marshall et al. |
| 5,789,538 A | 8/1998 | Rebar et al. |
| 5,912,173 A | 6/1999 | Leonard et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Aiuti, et at., "Lentiviral Hematopoietic Stem Cell Gene Therapy in Patients With Wiskott-Aldrich Syndrome," *Science* 23(341):6148 (2013) doi: 10.1126/science.1233151.

Argast, et al., "I-PPOL and I-CREL Homing Site Sequence Degeneracy Determined by Random Mutagenesis and Sequential in Vitro Enrichment," *J. Mol. Biol.* 280:345-353 (1998).

Ashworth, et al., "Computational Redesign of Endonuclease DNA Binding and Cleavage Specificity," *Nature* 441:656-659 (2006).

Beerli, et al., "Engineering Polydactyl Zinc-Finger Transcription Factors," *Nature Biotechnol.* 20:135-141(2002).

(Continued)

*Primary Examiner* — Michael Burkhart
(74) *Attorney, Agent, or Firm* — Pasternak Patent Law; Susan Abrahamson

(57) ABSTRACT

The present disclosure is in the field of genome engineering, particularly targeted integration of a functional SCID-related genes (e.g., IL2RG, RAG1 and/or RAG2 gene) into the genome of a cell for provision of proteins lacking or deficient in SCID.

9 Claims, 23 Drawing Sheets

(56) References Cited

U.S. PATENT DOCUMENTS

| | | | |
|---|---|---|---|
| 8,110,379 B2 | 2/2012 | DeKelver et al. | |
| 8,153,773 B2 | 4/2012 | Jemiely et al. | |
| 8,329,986 B2 | 12/2012 | Butler et al. | |
| 8,399,218 B2 | 3/2013 | Gupta et al. | |
| 8,409,861 B2 | 4/2013 | Guschin et al. | |
| 8,563,314 B2 | 10/2013 | Gregory et al. | |
| 8,586,526 B2 | 11/2013 | Gregory et al. | |
| 8,623,618 B2 | 1/2014 | Doyon et al. | |
| 8,697,359 B1 | 4/2014 | Zhang | |
| 8,703,489 B2 | 4/2014 | Wang | |
| 8,772,008 B2 | 7/2014 | Doyon | |
| 8,936,936 B2 | 1/2015 | Holmes et al. | |
| 8,945,868 B2 | 2/2015 | Collingwood et al. | |
| 8,956,828 B2 | 2/2015 | Bonini et al. | |
| 9,005,973 B2 | 4/2015 | Cost et al. | |
| 9,045,763 B2 | 6/2015 | DeKelver et al. | |
| 9,616,090 B2 * | 4/2017 | Conway | A61K 35/12 |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0267061 A1 | 12/2005 | Martin | |
| 2006/0063231 A1 | 3/2006 | Li et al. | |
| 2007/0117128 A1 | 5/2007 | Smith et al. | |
| 2008/0159996 A1 | 7/2008 | Ando et al. | |
| 2009/0068164 A1 | 4/2009 | Segal et al. | |
| 2010/0218264 A1 | 8/2010 | Cui et al. | |
| 2011/0016543 A1 | 1/2011 | Weinstein et al. | |
| 2011/0201055 A1 | 8/2011 | Doyon et al. | |
| 2011/0265198 A1 | 10/2011 | Gregory et al. | |
| 2012/0017290 A1 | 1/2012 | Cui et al. | |
| 2012/0195936 A1 | 8/2012 | Rudolph et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |
| 2013/0177983 A1 | 7/2013 | Rebar | |
| 2013/0196373 A1 | 8/2013 | Gregory et al. | |
| 2013/0253040 A1 | 9/2013 | Miller et al. | |
| 2014/0335063 A1 | 11/2014 | Cannon et al. | |
| 2015/0056705 A1 | 2/2015 | Conway et al. | |
| 2016/0030477 A1 | 2/2016 | Conway et al. | |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A1 | 8/2001 |
| WO | WO 01/88197 A1 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 07/014275 A2 | 2/2007 |
| WO | WO 10/079430 A1 | 7/2010 |

OTHER PUBLICATIONS

Belfort, et al., "Homing Endonucleases: Keeping the House in Order," *Nucleic Acids Research* 25:3379-3388 (1997).
Biancotti, et al., "Increasing Hematopoetic Stem Cell Yield to Develop Mice With Human Immune Systems," *Biomed Res. Int.* Epub vol. 2013, Article ID 740892, 11 pages. (2013).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From Xanthomonas campestris PV. vesicatoria," *Mol. Gen. Genet.* 218:127-136 (1989).
Cavazzana-Calvo, et al., "Gene Therapy of Human Severe Combined Immunodeficiency (SCID)-X1 Disease," *Science* 288:669-672 (2000).
Chevalier, et al., "Design, Activity, and Structure of a Highly Specific Artificial Endonuclease," *Molecular Cell* 10:895-905 (2002).
Choo, et al., "Advances in Zinc Finger Engineering," *Curr. Opin. Struct. Biol.* 10:411-416 (2000).
Christian, et al., "TAL Effector Nucleases Create Targeted DNA Double-Strand Breaks," *Genetics* epub 10.1534/genetics.110.120717.
Cong, et al., "Multiplex Genome Engineering Using CRISPR/CAS Systems," *Sciencexpress* 1/10.1126/science 1231143 (2013).
Dujon, et al., "Mobile Introns: Definition of Terms and Recommended Nomenclature," *Gene* 82:115-118 (1989).
Epinat, et al., "A Novel Engineered Meganuclease Induces Homologous Recombination in Yeast and Mammalian Cells," *Nucleic Acids Research* 31:2952-2962 (2003).
Fischer, et al., "Gene Therapy of Severe Combined Immunodeficiencies," *Nature Reviews Immunology* 2:615-621 (2002).
Freeman, et al., "Antimicrobial Prophylaxis for Primary Immunodeficiencies," *Current Opinion in Allergy and Clinical Immunology* 9:525-530 (2009).
Genovese, et al., "Targeted Genome Editing in Human Repopulating Haematopoietic Stem Cells," *Nature* 510:235-240 (2014) doi:10.1038/nature13420.
Gimble, et al., "Substrate Recognition and Induced DNA Distortion by the PI-SCEI Endonuclease, An Enzyme Generated by Protein Splicing," *J. Mol. Biol.* 263:163-180 (1996).
Guo, et al., "Directed Evolution of an Enhanced and Highly Efficient FOKI Cleavage Domain for Zinc Finger Nucleases," *J. Mol. Biol.* 400(1):96-107 (2010).
Guschin, et al., "A Rapid and General Assay for Monitoring Endogenous Gene Modification," *Methods Mol. Biol.* 649:247-256 (2010).
Hacein-Bey-Abina, et al., "Sustained Correction of X-Linked Severe Combined Immunodeficiency by Ex Vivo Gene Therapy," *NEJM* 346:1185-1193 (2002).
Hacein-Bey-Abina, et al., "Insertional Oncogenesis in 4 Patients After Retrovirus-Mediated Gene Therapy of SCID-X1," *J. Clin Investigation* 118(9): 3132-3142 (2008).
Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).
Heuer et al., "Repeat Domain Diversity of AVRBS3-Like Genes in Ralstonia solanacearum Strains and Association With Host Preferences in the Field," *Appl. And Envir. Micro.* 73(13):4379-4384 (2007).
Isalan, et al., "A Rapid, Generally Applicable Method to Engineer Zinc Fingers Illustrated by Targeting the HIV-1 Promoter," *Nat. Biotechnol.* 19:656-660 (2001).
Jansen, et al., "Identification of Genes That Are Associated With DNA Repeats in Prokaryotes," *Molecular Microbiology* 43(6):1565-1575 (2002).
Jasin, "Genetic Manipulation of Genomes With Rare-Cutting Endonucleases," *Trends Genet.* 12:224-228 (1996).
Kay, et al., "A Bacterial Effector Acts As a Plant Transcription Factor and Induces a Cell Size Regulator," *Science* 318:648-651 (2007).
Kormann, et al., "Expression of Therapeutic Proteins After Delivery of Chemically Modified MRNA in Mice," *Nature Biotechnology* 29(2):154-157 (2011).
Kutukculer, et al., "Novel Mutations and Diverse Clinical Phenotypes in Recombinase-Activating Gene 1 Deficiency," *It J of Ped* 38:8 (2012).
Lombardo, et al., "Gene Editing in Human Stem Cells Using Zinc Finger Nucleases and Integrase-Defective Lentiviral Vector Delivery," *Nat. Biotechnology* 25:1298-1306 (2007).
Makarova, et al.,"A DNA Repair System Specific for Thermophilic Archaea and Bacteria Predicted by Genomic Context Analysis," *Nucleic Acids Res.* 30:482-496 (2002).
Makarova, et al.,"A Putative RNA-Interference-Based Immune System in Prokaryotes: Computational Analysis of the Predicted

(56) References Cited

OTHER PUBLICATIONS

Enzymatic Machinery, Functional Analogies With Eukaryotic RNAI, and Hypothetical Mechanisms of Action," *Biol. Direct* 1:7 (2006).
Matthews, et al., "Compound Heterozygous Mutation of RAG1 Leading to Omenn Syndrome," *PLOS One* 10(4):e0121489 (2015)
.
Moscou, et al., "A Simple Cipher Governs DNA Recognition by TAL Effectors," *Science* 326:1501 (2009).
Nishana, et al., "Role of Recombination Activating Genes in the Generation of Antigen Receptor Diversity and Beyond Immunology," 137:271-281 (2012).
Olovnikov, et al., "Bacterial Argonaute Samples the Transcriptome to Identify Foreign DNA," *Mol. Cell.* 51(5):594-605 (2013).
Pabo, et al., "Design and Selection of Novel CYS2HIS2 Zinc Finger Proteins," *Ann. Rev. Biochem.* 70:313-340 (2001).
Paques, et al., "Meganucleases and DNA Double-Strand Break-Induced Recombination: Perspectives for Gene Therapy," *Current Gene Therapy* 7:49-66 (2007).
Perez, et al., "Establishment of HIV-1 Resistance in CD4+ T Cells by Genome Editing Using Zinc-Finger Nucleases," *Nature Biotechnology* 26:808-816 (2008).
Perler, et al., "Protein Splicing Elements: Inteins and Exteins a Definition of Terms and Recommended Nomenclature," *Nucleic Acids Research* 22:1125-1127 (1994).
Philippe, et al., "Lentiviral Vectors With a Defective Integrase Allow Efficient and Sustained Transgene Expression In Vitro and In Vivo," *Proc. Nat'l. Acad. Sci. USA* 103(47):17684-17689 (2006).
Ran, et al., "In Vivo Genome Editing Using *Staphylococcus aureus* CAS9," *Nature* 520:186-194 (2015).
Schornack, et al., "Gene-For-Gene-Mediated Recognition of Nuclear-Targeted AVRBS3-Like Bacterial Effector Proteins," *J. Plant Physiol.* 163(3):256-272 (2006).
Segal, et al., "Custom DNA-Binding Proteins Come of Age: Polydactyl Zinc-Finger Proteins," *Curr. Opin. Biotechnol.* 12:632-637 (2001).
Sheng, et al., "Structure-Based Cleavage Mechanism of Thermus thermophilus Argonaute DNA Guide Strand-Mediated DNA Target Cleavage," *Proc. Natl. Acad. Sci. USA* 111(2):652-657 (2013) doi: 10.1073/pnas.1321032111.
Swarts, et al., "DNA-Guided DNA Interference by a Prokaryotic Argonaute," *Nature* 507(7491):258-261 (2014).
Tebas, et al., "Gene Editing of CCR5 in Autologous CD4 T Cells of Persons Infected With HIV," *New Engl. J. Med.* 370(10):901 (2014).
Urnov, et al., "Highly Efficient Endogenous Human Gene Correction Using Designed Zinc- Finger Nucleases," *Nature* 435(7042):646-651(2005).
Urnov, et al., "Genome Editing With Engineered Zinc Finger Nucleases," *Nature* 11:636-646 (2010).
Vickers, "Severe Combined Immune Deficiency: Early Hospitalisation and Isolation," Chapter 3, pp. 29-27, ISBN 978-0-470-31986-4 (2009).
Vogel, "A Bacterial Seek-and-Destroy System for Foreign DNA," *Science* 344(6187):972-973 (2014) doi: 10.1126/science.1252962.
Villa, et al., "V(D)J Recombination Defects in Lymphocytes Due to RAG Mutations: Severe Immunodeficiency With a Spectrum of Clinical Presentations," *Blood* 97(1):81-88 (2001).
Yang, et al., "Purification, Cloning, and Characierization of the Cel I Nuclease," Biochemistry 39:3533-3541 (2000).
Yu, et al., "An Engineered VEGF-Activating Zinc Finger Protein Transcription Factor Improves Blood Flow and Limb Salvage in Advanced-Age Mice," *FASEB J.* 20:479-481 (2006).
Yuan, et al., "Crystal Siructure of A. aeolicus Argonaute, a Site-Specific DNA-Guided Endoribonuclease, Provides Insights Into RISC-Mediated MRNA Cleavage," *Molecular Cell* 19:405-419 (2005) doi: 10.1016/j.molcel.2005.07.011.

\* cited by examiner

| samplename | %indels | samplename | %indels | samplename | %indels | samplename | %indels |
|---|---|---|---|---|---|---|---|
| 44206:44197 | 45.6 | 44248:44237 | 56.9 | 44298:44271 | 42.8 | 44328:44310 | 21.9 |

| samplename | %indels | samplename | %indels | samplename | %indels | samplename | %indels |
|---|---|---|---|---|---|---|---|
| 44206:44197 | 45.6 | 44248:44237 | 56.9 | 44298:44271 | 42.8 | 44328:44310 | 21.9 |
| 44207:44188 | 43.6 | 44248:44233 | 56.7 | 44298:44281 | 39.9 | 44330:44308 | 21.5 |
| 44206:44201 | 42.7 | 44247:44233 | 56.0 | 44296:44271 | 36.1 | 44330:44316 | 21.2 |
| 44207:44201 | 41.6 | 44244:44233 | 52.6 | 44287:44274 | 34.8 | 44328:44308 | 20.0 |
| 44206:44192 | 41.5 | 44244:44236 | 51.8 | 44288:44271 | 34.8 | 44330:44307 | 19.9 |
| 44206:44188 | 40.2 | 44248:44236 | 47.9 | 44287:44271 | 32.5 | 44328:44307 | 19.5 |
| 44207:44197 | 40.1 | 44248:44226 | 47.2 | 44298:44275 | 32.5 | 44330:44310 | 19.5 |
| 44215:44188 | 38.8 | 44244:44237 | 46.7 | 44288:44275 | 31.2 | 44334:44308 | 19.0 |
| 44220:44188 | 38.7 | 44247:44237 | 45.6 | 44288:44274 | 30.6 | 44331:44307 | 18.6 |
| 44207:44192 | 36.7 | 44247:44226 | 43.5 | 44287:44275 | 29.4 | 44334:44310 | 18.4 |
| 44220:44192 | 36.0 | 44245:44226 | 41.9 | 44296:44281 | 27.8 | 44334:44307 | 18.1 |
| 44220:44197 | 36.0 | 44247:44236 | 40.8 | P41552:P41553 | 27.4 | 44334:44316 | 18.1 |
| 44220:44201 | 34.8 | 44245:44236 | 40.5 | 44298:44274 | 26.8 | 44328:44316 | 18.1 |
| 44215:44192 | 34.4 | 44245:44237 | 39.5 | 44288:44281 | 26.8 | 44331:44316 | 17.2 |
| 44215:44201 | 33.9 | 44244:44226 | 37.0 | 44296:44274 | 22.3 | 44331:44310 | 16.5 |
| 44215:44197 | 33.5 | P41513:P41514 | 36.9 | 44296:44275 | 22.3 | P41556:P41558 | 15.5 |
| P41511:P41512 | 30.5 | GFP | 0.2 | GFP | 0.2 | 44331:44308 | 13.0 |
| GFP | 0.0 | | | | | GFP | 0.2 |

| samplename | %indels |
|---|---|
| 44364:44357 | 43.6 |
| 44373:44357 | 40.8 |
| 44373:44350 | 40.1 |
| 44370:44357 | 38.6 |
| 44364:44355 | 37.7 |
| 44370:44355 | 36.2 |
| 44364:44350 | 35.9 |
| 44373:44355 | 35.2 |
| 44366:44357 | 34.5 |
| 44364:44348 | 33.3 |
| 44373:44348 | 32.4 |
| 44370:44350 | 31.5 |
| 44370:44348 | 31.2 |
| 44366:44355 | 29.5 |
| 44366:44350 | 29.1 |
| 44366:44348 | 28.1 |
| P41561:P41562 | 17.4 |
| GFP | 0.2 |

FIGURE 3B

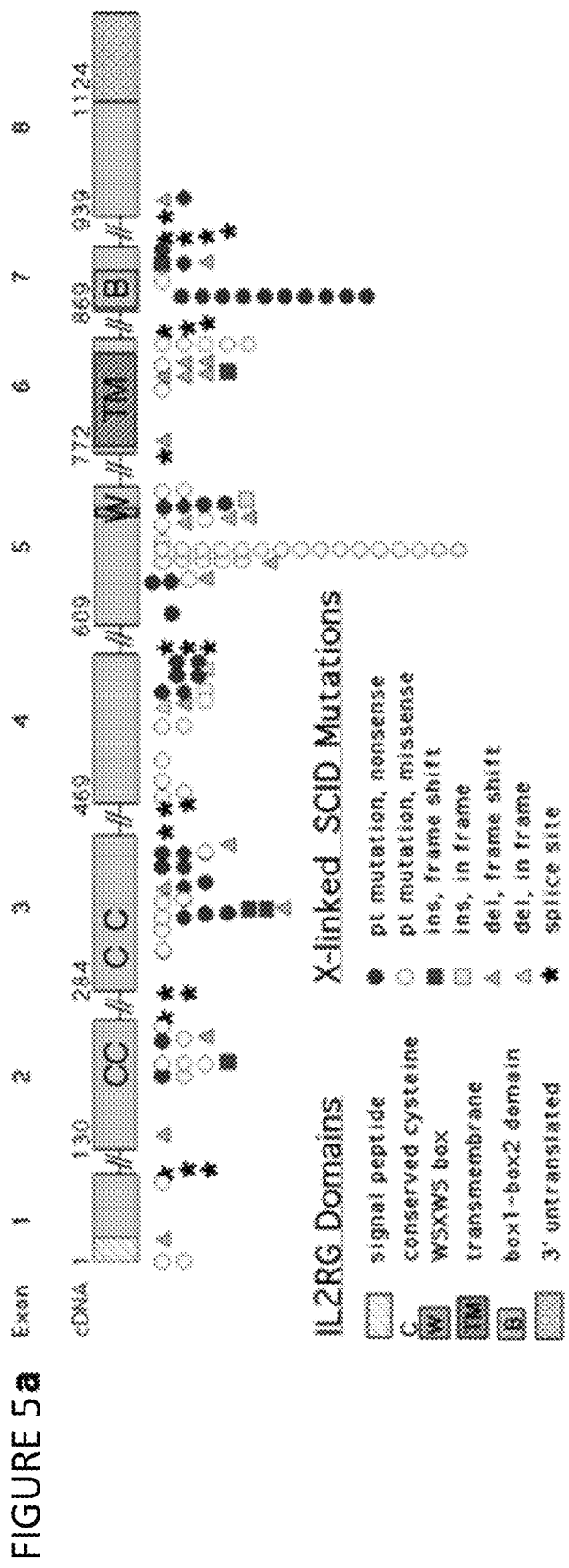
FIGURE 5a
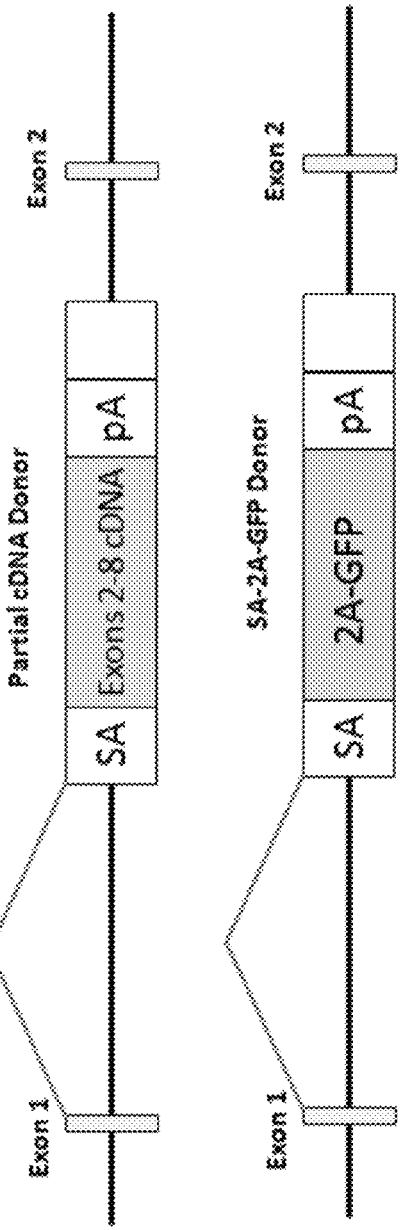
FIGURE 5b
FIGURE 5c

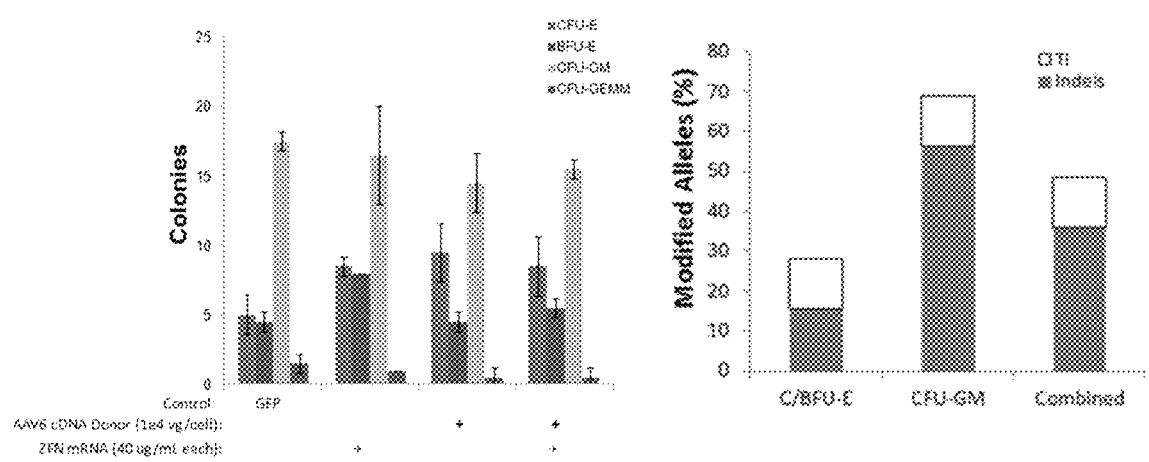
FIGURE 13A                    FIGURE 13B

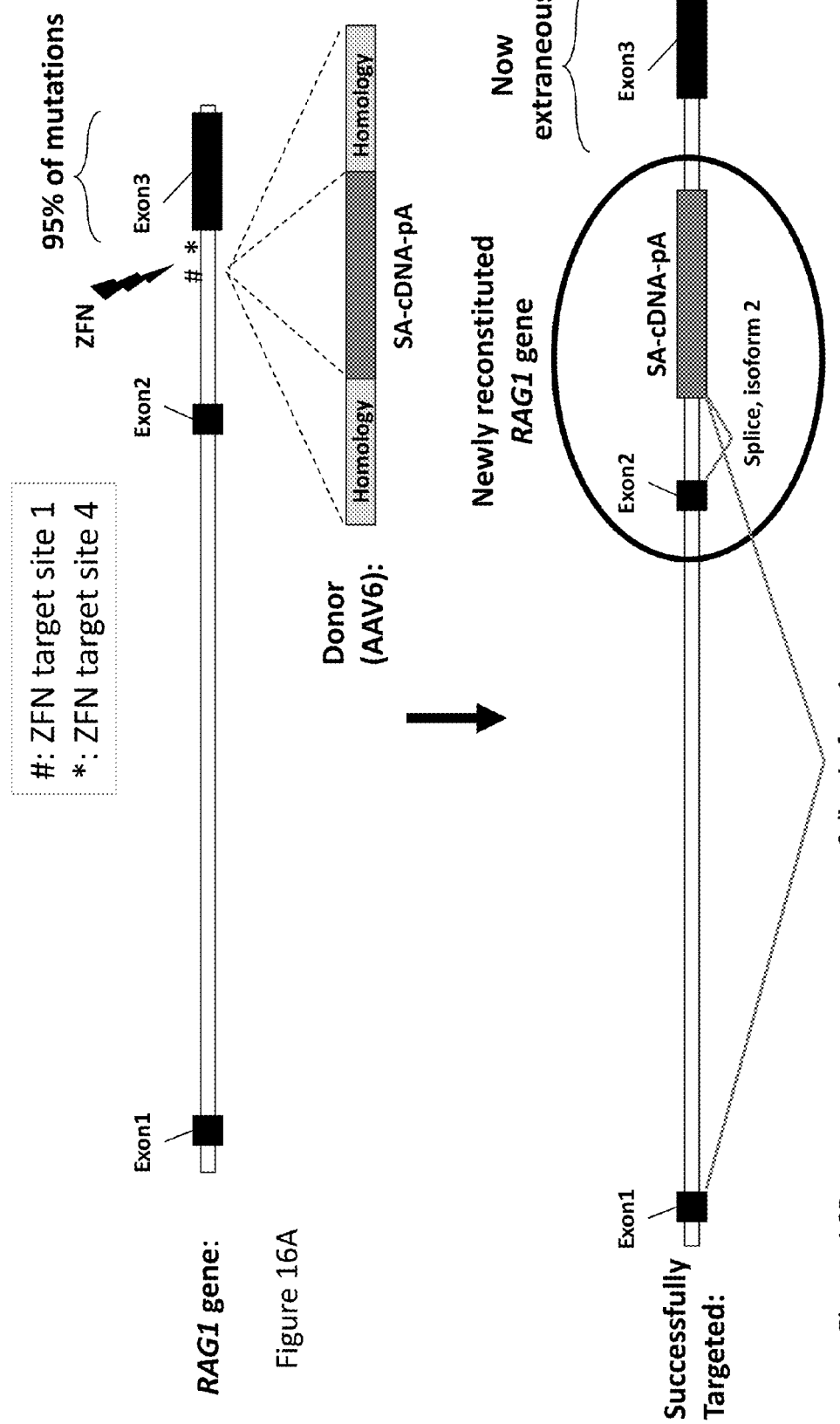

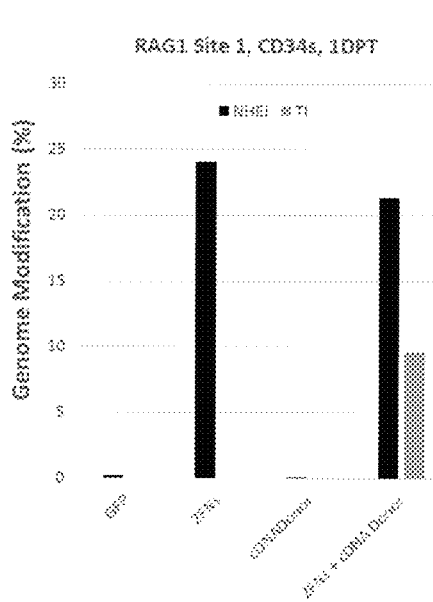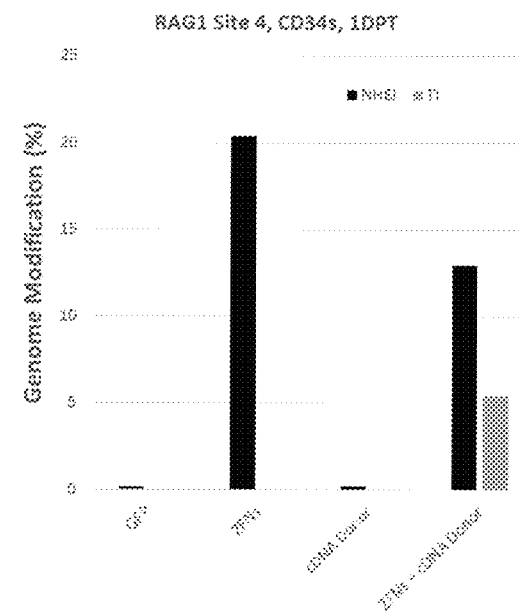
Figure 18A
Figure 18B

SEQUENCE LISTING

```
<160> NUMBER OF SEQ ID NOS: 101

<210> SEQ ID NO 1
<211> LENGTH: 25
<212> TYPE: DNA
<213> ORGANISM: Homo sapiens

<400> SEQUENCE: 1
ctgacctctt ctcttcctcc cacag                                       25

<210> SEQ ID NO 2
<211> LENGTH: 13
<212> TYPE: DNA
<213> ORGANISM: Homo sapiens
```

<400> SEQUENCE: 2
tttctctcca cag                                                          13

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Arg Ser Cys Arg Ser Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Arg Ser Ala Leu Ser Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Gly Ser Leu Thr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Ser His Leu Thr Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Leu Asp Trp Leu Pro Met
1               5

<210> SEQ ID NO 8
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 8

Gln Ser Gly Asp Leu Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Ala Asp Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Arg Ser Asn Leu Asp Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Ala Asn Leu Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Ala Asn Arg Thr Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg His His Leu Thr Arg
1               5
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Arg His Asn Leu Arg Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Asp Ala Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Gly Asn Leu Thr Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp His Leu Ser Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Ser Arg Tyr Leu Met Val
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly His Leu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Lys Trp Thr Leu Gln Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Asp Asp Leu Thr Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Arg Ser Thr Arg Arg Gln
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Ser Asp Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Asn Asp Leu Asn Ser
1               5

<210> SEQ ID NO 25
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Asp Ser Leu Leu Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Tyr Asp Arg Phe Gln
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ser Gly Asn Leu Ala Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Asp His Leu Ser Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Ala Arg Thr Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Arg Ser Thr Arg Ile Thr
```

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Asn Ala Thr Arg Ile Asn
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Met Tyr Thr Leu Ser Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Asp Ala Leu Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Arg Gly Thr Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp Ala Leu Thr Gln
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 36

Gln Ser Gly Ala Leu Ala Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Lys Ser Ala Arg Ala Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Leu His His Leu Asn Asn
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Arg Ile Ser Leu Ala Ala
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ser Asp Asn Leu Ser Ala
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Gln Asn Arg Thr Arg
1               5

<210> SEQ ID NO 42
```

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Gln Gly Val Leu Thr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ser Asp Asn Leu Arg Glu
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp His Leu Ser Gln
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Ser Ala Asn Arg Thr Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Asn Gly Leu Thr Gln
1               5

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
ccctgggtgt agtctgtctg tgtcagga                                              28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atgaagagca agcgccatgt tgaagcca                                              28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ataagaggga tgtgaatggt aatgatgg                                              28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctgcagctgc ccctgctggg agtggggc                                              28

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggccagtggc aggcaccaga tctctgta                                              28

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttacaatcat gtgggcagaa ttgaaaag                                              28

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgtaatggcc agtggcaggc accagatc                                              28
```

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcatgtgggc agaattgaaa agtggagt                                          28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tgattgtaat ggccagtggc aggcacca                                          28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gtgggcagaa ttgaaaagtg gagtggga                                          28

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gccagtggca ggcaccagat ctctgtac                                          28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttacaatcat gtgggcagaa ttgaaaag                                          28

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gtacagagat ctggtgcctg c                                                 21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
attctgccca catgattgta a                                              21

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Arg Ser Asn Leu Val Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Ser Gly Ser Leu Thr Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gly Cys Asn Leu Gly Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Arg Ser Asn Leu Thr Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Trp Ser Thr Ser Leu Arg Ala
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Leu Ser Ser Leu Ser Ala
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Arg Ser Asn Leu Ser Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

His Arg Gln His Leu Val Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Arg Ser Thr Leu Arg Gln
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ser Ser Asn Leu Ala Arg
1               5

<210> SEQ ID NO 71
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 71

Gln Gly Cys Asn Leu Val Lys
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Arg Gln Asn Leu Val Ala
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

His Arg His His Leu Gly Gln
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Asn Ala Thr Arg Thr Lys
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg His Trp Ser Leu Ser Val
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Arg Thr Asn Leu Val Glu
1               5
```

```
<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Ser Lys Thr Arg Thr Asn
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ser Asp Val Leu Ser Thr
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Thr Ala Ala Leu Ser Tyr
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Leu Ala Asn Leu Gln Thr
1               5

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: a, c, t, g, unknown or other

<400> SEQUENCE: 81
tgtgtacaga ctaagttgaa gatgttan                                      28

<210> SEQ ID NO 82
<211> LENGTH: 28
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 82
ttccaagtaa taactgtgtg ctcaagtg                                           28

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cttttatgac ccatttggaa gaaataaa                                           28

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
atgataaagc tgcaaaccca aagaaact                                           28

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cacatgattg taatggccag tgg                                                23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ttctgcccac atgattgtaa tgg                                                23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cactggccat tacaatcatg tgg                                                23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
ttgagcacac agttattact tgg                                              23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tcttccaaat gggtcataaa agg                                              23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ctgcgctcaa ggctggagct tgg                                              23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cccagactag tgattagctg tgg                                              23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tcccagctcc ttggatggaa tgg                                              23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aaccgctacc ctggtattgc tgg                                              23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 94
taattctgta gtaagtaagc agg                                              23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aatatacaac tgagggagac agg                                              23

<210> SEQ ID NO 96
<211> LENGTH: 9
<212> TYPE: PRT
<213> ORGANISM: Unknown
<220> FEATURE:
<223> OTHER INFORMATION: Description of Unknown: "LAGLIDADG" family
      homing endonuclease peptide

<400> SEQUENCE: 96

Leu Ala Gly Leu Ile Asp Ala Asp Gly
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Pro Ala Asn Leu Thr Arg
1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Gly Glu Lys Pro
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Gly Glu Arg Gly
1               5

<210> SEQ ID NO 100
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 100

Thr Gly Ser Gln Lys Pro
1               5

<210> SEQ ID NO 101
<211> LENGTH: 800
<212> TYPE: DNA
<213> ORGANISM: Homo sapiens

<400> SEQUENCE: 101
gcccgtgtca cacagcacat atttgccaca ccctctgtaa agccctggtt tataaggttc    60
tttccaccgg aagctatgac agaggaaacg tgtgggtggg gaggggtagt gggtgaggga   120
cccaggttcc tgacacagac agactacacc cagggaatga agagcaagcg ccatgttgaa   180
gccatcatta ccattcacat ccctcttatt cctgcagctg ccctgctgg gagtggggct    240 gaacacgaca attctgacgc ccaatgggaa tgaagacacc acagctggtg ggaaatctgg   300
gactggaggg ggctggtgag aagggtggct gtgggaaggg gccgtacaga gatctggtgc   360
ctgccactgg ccattacaat catgtgggca gaattgaaaa gtggagtggg aagggcaagg   420
gggagggttc cctgcctcac gctacttctt ctttctttct tgtttgtttg tttctttctt   480
tcttttgagg cagggtctca ctatgttgcc taggctggtc tcaaactcct ggcctctagt   540
gatcctcctg cctcagcctt tcaaagcacc aggattacag acatgagcca ccgtgcttgg   600
cctcctcctt ctgaccatca tttctctttc cctccctgcc ttcattttct ccccaatcta   660
gatttcttcc tgaccactat gcccactgac tccctcagtg tttccactct gcccctccca   720
gaggttcagt gttttgtgtt caatgtcgag tacatgaatt gcacttggaa cagcagctct   780
gagccccagc ctaccaacct                                               800
```

GENE CORRECTION OF SCID-RELATED GENES IN HEMATOPOIETIC STEM AND PROGENITOR CELLS

CROSS-REFERENCE TO RELATED APPLICATIONS

The present application is a continuation of U.S. patent application Ser. No. 14/813,924, filed Jul. 30, 2015, which claims the benefit of U.S. Provisional Application No. 62/030,942, filed Jul. 30, 2014, the disclosure of which is hereby incorporated by reference in its entirety.

TECHNICAL FIELD

The present disclosure is in the field of genome engineering, particularly targeted modification of the genome of a cell, including targeted integration of a corrective transgene of a mutant SCID-related gene (e.g., IL2R-gamma (IL2RG) and/or recombination activating genes (RAG genes such as RAG1, RAG2)).

BACKGROUND

Recombinant transcription factors comprising the DNA binding domains from zinc finger proteins ("ZFPs") or TAL-effector domains ("TALEs") and engineered nucleases including zinc finger nucleases ("ZFNs"), TALENs, CRISPR/Cas nuclease systems, and homing endonucleases that are all designed to specifically bind to target DNA sites have the ability to regulate gene expression of endogenous genes and are useful in genome engineering and gene therapy. See, e.g., U.S. Pat. Nos. 9,045,763; 9,005,973; 8,956,828; 8,945,868; 8,586,526; 8,329,986; 8,399,218; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 20100218264; 20120017290; 20110265198; 20130137104; 20130122591; 20130177983 and 20130177960 and 20150056705, the disclosures of which are incorporated by reference in their entireties for all purposes. Further, targeted nucleases are being developed based on the Argonaute system (e.g., from *T. thermophilus*, known as 'TtAgo', see Swarts et al (2014) *Nature* 507 (7491): 258-261), which also may have the potential for uses in genome editing and gene therapy.

Nuclease-mediated gene therapy can be used to genetically engineer a cell to have one or more inactivated genes and/or to cause that cell to express a product not previously being produced in that cell (e.g., via transgene insertion and/or via correction of an endogenous sequence). Examples of uses of transgene insertion include the insertion of one or more genes encoding one or more novel therapeutic proteins, insertion of a coding sequence encoding a protein that is lacking in the cell or in the individual, insertion of a wild-type gene in a cell containing a mutated gene sequence, and/or insertion of a sequence that encodes a structural nucleic acid such as shRNA or siRNA. Examples of useful applications of 'correction' of an endogenous gene sequence include alterations of disease-associated gene mutations, alterations in sequences encoding splice sites, alterations in regulatory sequences and targeted alterations of sequences encoding structural characteristics of a protein. Transgene construct(s) is(are) inserted by either homology directed repair (HDR) or by end capture during non-homologous end joining (NHEJ) driven processes. See, e.g., U.S. Pat. Nos. 9,045,763; 9,005,973; 7,888,121 and 8,703,489.

Clinical trials using these engineered transcription factors and nucleases have shown that these molecules are capable of treating various conditions, including cancers, HIV and/or blood disorders (such as hemoglobinopathies and/or hemophilias). See, e.g., Yu et al. (2006) *FASEB J.* 20:479-481; Tebas et al (2014) *New Eng J Med* 370(10):901. Thus, these approaches can be used for the treatment of diseases.

Severe combined immunodeficiency (SCID) is a heterogeneous group of primary immunodeficiencies comprising at least 11 different conditions (Kutukculer et al (2012) *It J of Ped* 38:8). All patients with SCID are susceptible to infections from common bacteria and viruses as well as opportunistic and fungal pathogens. X-linked severe combined immunodeficiency (X-SCID) is an immunodeficiency disorder in which the body produces very few T cells and natural killer cells. In the absence of T cell help, B cells become defective (Fisher et al. (2002) *Nature Reviews* 2:615-621). It is an X-linked recessive trait such that nearly all patients are male, and stems from a mutated version of the IL2RG gene (also referred to as the "common gamma" gene or "common cytokine receptor gamma chain"), located at xq13.1 on the X-chromosome. The common gamma protein is shared between receptors for IL-2, IL-4, IL-7, IL-9, IL-15 and IL-21, leaving X-SCID patients unable to develop functional T and NK cells. Persons afflicted with X-SCID often have infections very early in life, before three months of age. This occurs due to the decreased amount of immunoglobulin G (IgG) levels in the infant during the three-month stage. This is followed by viral infections such as pneumonitis, an inflammation of the lung which produces common symptoms such as cough, fever, chills, and shortness of breath. Recurrent eczema-like rashes are also a common symptom. Other common infections experienced by individuals with X-SCID include diarrhea, sepsis, and otitis media. Some other common symptoms that are experienced by X-SCID patients include failure to thrive, gut problems, skin problems, and muscle hypotonia (Vickers *Severe Combined Immune Deficiency: Early Hospitalisation and Isolation* (2009) pp. 29-47. ISBN 978-0-470-31986-4). Without therapeutic and/or environmental intervention, X-SCID is typically fatal during the first year of life (Hacein-Bey-Abina et al, (2002) *NEJM* 346: 1185-1193).

Another type of SCID is related to defects in the recombination activating genes (RAG1, RAG2), where approximately 10% of all SCID cases are tied to RAG1 or RAG2 (Ketukculer, ibid). The protein products of the RAG1 and RAG2 genes (Rag1 and Rag2, respectively) are essential for V(D)J rearrangement in B and T cell receptors, and thus are required for proper development of B cells and T cells and are also thought to be involved in inflammation (see, e.g., U.S. Patent Publication No. 20110016543). Together, Rag1 and Rag2 initiate V(D)J recombination by cleaving DNA to generate double strand breaks which are then repaired by the NHEJ machinery.

Omenn Syndrome is an autosomal recessive variant of SCID with distinctive clinical features of generalized erythodermia, hepatosplenomegaly and lymphadenopathy. Unlike patients with classic SCID, patients with Omenn Syndrome have circulating T cells with an abnormal phenotype: they are typically poorly reactive, oligoclonal, and display cell-surface markers of previous activation. B cells are typically absent or low and IgG levels are generally low while IgE levels are high (Matthews et al (2015) *PLoS One* 10(4):e0121489). Omenn Syndrome is typically caused by mutations in RAG1 or RAG2 although mutations in other genes can also lead to it. Generally, hypomorphic RAG mutations, sometimes in combination with RAG null mutations, lead to Omenn Syndrome (Matthews, ibid).

Currently, there are three types of treatments available for SCID patients, namely, the use of medication, sterile environments, and intravenous immunoglobulin therapy (IVIG). First, antibiotics or antivirals are administered to control opportunistic infections, such as fluconazole for candidiasis, and acyclovir to prevent herpes virus infection (Freeman et al. *Current Opinion in Allergy and Clinical Immunology* (2009) 9 (6):525-530). In addition, the patient can also undergo intravenous immunoglobulin (IVIG) supplementation. However, the IVIG is expensive, in terms of both time and money. In addition, the aforementioned treatments only serve to prevent opportunistic infections, and are by no means a cure for X-SCID or other SCID disorders.

At present, bone marrow transplantation (BMT) is the standard curative procedure and results in a full immune reconstitution, if an appropriate donor can be identified and if the engraftment is successful. A bone marrow transplant requires an acceptable human leukocyte antigen (HLA) match between the donor and the recipient. As the array of HLA molecules is different between individuals, cells of the immune system can utilize the HLA apparatus to distinguish self from foreign cells. A BMT can be allogeneic (donor and recipient are different people) or autologous (donor and recipient are the same person). An autologous BMT therefore has a full HLA match, whereas, a match for an allogenic BMT is more complicated. In standard practice, an allogenic graft is better when all 6 of the known major HLA antigens are the same—a 6 out of 6 match. Patients with a 6/6 match have a lower chance of graft-versus-host disease, graft rejection, having a weak immune system, and getting serious infections. For bone marrow and peripheral blood stem cell transplants, sometimes a donor with a single mismatched antigen is used—a 5 out of 6 match. Therefore, a BMT may result in a full immune reconstitution and thus be curative in an X-SCID patient, but potential complications limit efficacy and widespread use. For patients with Omenn Syndrome, BMT is also the preferred method of treatment however Omenn Syndrome patients have a higher rate of mortality following BMT than other SCID patients.

Previous gene therapy clinical trials for X-SCID patients have used retroviral vectors comprising a wild type IL2RG gene (Cavazzana-Calvo et al. (2000) *Science* 288(5466): 669-72). Retroviral vectors randomly integrate into the host genome, however, and thus can cause insertional oncogenesis in patients when integration occurs in proto-oncogenes (Hacein-Bey-Abina et al. (2008) *J. Clin Investigation* 118 (9):3132-42). The majority of patients undergoing this therapy developed leukemia as a result of this insertional oncogenesis, thus this method is not a safe and effective therapy.

The development of integrase-deficient lentiviral vectors (IDLV) (Philippe et al. (2006) *Proc. Nat'l Acad. Sci.* 103 (47):17684-9), or IDLV, has facilitated further investigation of gene correction of IL2RG for X-SCID due to its inability to integrate into the host genome. The ability of zinc finger nucleases (ZFNs), transcription activator-like effector nucleases (TALENs), CRISPR/Cas systems and TtAgo to target a specific region of DNA, introduce a targeted double stranded break, which then facilitates targeted integration of an introduced transgene makes this genome editing technology highly attractive in the development of a potential curative treatment.

To this end, investigators have targeted exon 5 of the endogenous IL2RG locus for ZFN cleavage and subsequent TI of IDLV-delivered corrective IL2RG cDNA in hematopoietic stem and progenitor cells (HSPCs). See, e.g., U.S. Pat. Nos. 7,888,121 and 7,951,925; Lombardo et al. (2007) *Nat Biotech* 25(11):1298-306; Genovese et al. (2014) *Nature* 510(7504):235-40. However, these methods may have potential disadvantages in that introducing a transgene in the middle of an exon creates a partially transcribed region upstream of the introduced transgene, which may interfere with the activity of the introduced corrective gene. Furthermore, the delivered episomal transgene may still be able to randomly integrate into the genome if another viral integrase is present in the cell. Immunosuppressed patients (such as all X-SCID patients are) might have activation of endogenous retroviruses, thus barring patients who are also HIV positive from receiving virally delivered gene therapy for X-SCID treatment.

Thus, there remains a need for additional strategies of IL2RG and RAG gene correction and transgene donor delivery for treatment and/or prevention of SCID.

SUMMARY

The present invention describes compositions and methods for use in gene therapy and genome engineering. Specifically, the methods and compositions described relate to targeted insertion of a transgene (donor) including protein-encoding sequence, for example a protein that is lacking or deficient in a subject with a SCID. In certain embodiments, targeted integration of corrective SCID-related gene cassette (e.g., IL2RG and/or RAG (RAG1 and/or RAG2)) into the genome of a cell (e.g., hematopoietic stem cell with mutant versions of the SCID-related gene) using highly specific DNA binding proteins (ZFNs, TALENs, CRISPR/Cas systems). The SCID-related gene cassettes (e.g., functional IL2RG and/or a RAG transgene) integrated into the targeted gene (e.g., IL2RG, RAG1, RAG2, HPRT, etc.) may be carried on a viral or non-viral vector (e.g., adeno-associated viral (AAV)) and/or may be integrated using one or more nucleases.

In one aspect, described herein is a zinc-finger protein (ZFP) that binds to target site in an IL2RG or RAG gene in a genome, wherein the ZFP comprises one or more engineered zinc-finger binding domains. In one embodiment, the ZFPs are a pair of zinc-finger nucleases (ZFNs) that dimerize and then cleave a target genomic region of interest, wherein the ZFNs comprise one or more engineered zinc-finger binding domains and a nuclease cleavage domain or cleavage half-domain. In another aspect, described herein is a TALE protein (Transcription activator like effector) that binds to target site in an IL2RG or RAG gene in a genome, wherein the TALE comprises one or more engineered TALE DNA binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains of ZFNs and/or TALENs can be obtained, for example, from various restriction endonucleases and/or homing endonucleases. In one embodiment, the cleavage half-domains are derived from a Type IIS restriction endonuclease (e.g., Fok I). In certain embodiments, the zinc finger or TALE DNA binding domain recognizes a target site in an IL2RG or RAG gene, for example in intron 1. In certain embodiments, the target site is as shown in Tables 2 or 4. In certain embodiments the ZFN comprises a zinc finger protein having the recognition helix regions of the order as shown in Table 1. In other embodiments, the TALEN comprises a TALE protein having the RVDs shown in Table 3. In still further embodiments, a CRISPR/Cas nuclease system that targets an IL2RG or RAG gene is described, for example a CRISPR/Cas nuclease system comprising a guide RNA that associates with a nuclease (cleavage) domain to form an active nuclease. In certain embodiments, the guide RNA of the CRISPR/Cas system is shown in Table 5. In still further embodiments, a TtAgo system is used to effect cleavage. In preferred certain embodiments, the nuclease targets an intron (e.g., intron 1 or 2) of an IL2RG gene of a RAG gene. In other preferred certain embodiments, the nuclease targets intron 2 of a RAG gene (e.g., RAG1 or a RAG2 gene). In especially preferred embodiments, the nuclease targets the IL2RG2 gene within intron 1 and the RAG1 gene at chromosome 11, at position 36,590,551-36,590,578 and 36,590,581-36,590,607 (site 1) or 36,594,301-36,594,328 and 36,594,330-36,594,357 (site 4, where numbers are relative to UCSC GRCh37/hg19 human genome assembly.

The nuclease may bind to and/or cleave an IL2RG or RAG gene within the coding region of the gene or in a non-coding sequence within or adjacent to the gene, such as, for example, a leader sequence, trailer sequence or intron, or within a non-transcribed region, either upstream or downstream of the coding region.

In another aspect, described herein are compositions comprising one or more of the nucleases (ZFNs, TALENs, TtAgo and/or CRISPR/Cas systems) described herein, including a nuclease comprising a DNA-binding molecule (e.g., ZFP, TALE, sgRNA, etc.) and a nuclease (cleavage) domain. In certain embodiments, the composition comprises one or more nucleases in combination with a pharmaceutically acceptable excipient. In some embodiments, the composition comprises two or more sets (pairs) of nucleases, each set with different specificities. In other aspects, the composition comprises different types of nucleases. In some embodiments, the composition comprises polynucleotides encoding IL2RG-, RAG-specific nucleases, while in other embodiments, the composition comprises IL2RG-, RAG-specific nuclease proteins. In still further embodiments, the composition comprises one or more donor molecules, for example donors that encode a functional IL2RG, Rag1 and/or Rag2 protein(s), including any functional fragment thereof. In preferred embodiments, the donor comprises a partial IL2RG and/or RAG (e.g., RAG1 or RAG2) gene. Also preferred is a donor comprising a cDNA comprising exons 2 through 8 of the wild type IL2RG gene. Another preferred donor is a cDNA comprising exon 3 of a wild type RAG (RAG1 and/or RAG2) gene.

In another aspect, described herein is a polynucleotide encoding one or more nucleases or nuclease components (e.g., ZFNs, TALENs, TtAgo or nuclease domains of the CRISPR/Cas system) described herein. The polynucleotide may be, for example, mRNA or DNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012-0195936). In another aspect, described herein is a nuclease expression vector comprising a polynucleotide, encoding one or more ZFNs, TALENs, TtAgo or CRISPR/Cas systems described herein, operably linked to a promoter. In one embodiment, the expression vector is a viral vector, for example an AAV vector.

In another aspect, described herein is a host cell comprising one or more nucleases and/or nuclease expression vectors. In certain embodiments, the host cell includes a mutant version of one or more SCID-related genes (e.g., IL2RG and/or RAG gene) such that integration of the SCID-related gene cassette provides a functional version of the protein lacking or deficient in the cell. The host cell may be stably transformed or transiently transfected or a combination thereof with one or more nuclease expression vectors. In one embodiment, the host cell is a hematopoietic stem cell. In other embodiments, the one or more nuclease expression vectors express one or more nucleases in the host cell. In another embodiment, the host cell may further comprise an exogenous polynucleotide donor sequence (e.g., encoding an IL2RG or Rag protein). In any of the embodiments, described herein, the host cell can comprise an embryo cell, for example a one or more mouse, rat, rabbit or other mammal cell embryo (e.g., a non-human primate). In some embodiments, the host cell comprises a tissue. Also described are cells or cell lines descended from the cells described herein, including pluripotent, totipotent, multipotent or differentiated cells comprising a modification (e.g., integrated donor sequence) in an intron of an endogenous IL2RG and/or RAG gene (e.g., intron 1 of an endogenous IL2RG, or in intron 2 of an endogenous RAG1 or RAG2 gene). In certain embodiments, described herein are differentiated cells as described herein comprising a modification (e.g., integrated donor sequence) in an intron of an endogenous IL2RG and/or RAG gene (e.g., intron 1 of an endogenous IL2RG, or in intron 2 of an endogenous RAG1 or RAG2 gene), which differentiated cells are descended from a stem cell as described herein.

In another aspect, described herein is a method for cleaving an IL2RG and/or RAG gene in a cell, the method comprising: (a) introducing, into the cell, one or more polynucleotides encoding one or more nucleases that target one or more IL2RG and/or RAG (RAG1 or RAG2) genes under conditions such that the nuclease(s) is(are) expressed and the one or more IL2RG and/or RAG (RAG1 or RAG2) genes are cleaved.

In other embodiments, a genomic sequence in the target IL2RG and/or RAG (RAG1 or RAG2) gene is cleaved, for example using a nuclease (or vector encoding the nuclease) as described herein and a "donor" sequence inserted into the gene following targeted cleavage with the ZFN, TALEN, TtAgo or CRISPR/Cas system such that the donor sequence is expressed in the cell. The donor sequence may encode a functional IL2RG or Rag protein. In some embodiments, the donor sequence comprises a partial IL2RG and/or RAG (RAG1 or RAG2) gene sequence. In preferred embodiments, the donor comprises a partial cDNA of the IL2RG gene sequence comprising exons 2 through 8, or a full cDNA of the RAG1 gene comprising exon 3, or a full cDNA of the RAG2 gene comprising exon 3. Furthermore, the donor sequence may be present in the nuclease delivery system (e.g., non-viral vector or viral vector), present in a separate delivery mechanism (e.g., nuclease delivered in mRNA form and donor delivered using viral vector such as AAV) or, alternatively, may be introduced into the cell using a separate and/or different nucleic acid delivery mechanism. Insertion of a donor nucleotide sequence into the IL2RG and/or RAG (RAG1 or RAG2) locus can result in the expression of the transgene under control of the endogenous IL2RG and/or RAG (RAG1 or RAG2) genetic control elements, respectively. In some aspects, insertion of the transgene of interest results in expression of an intact exogenous protein sequence and lacks any IL2RG and/or RAG (RAG1 or RAG2)-encoded amino acids. In other aspects, the expressed exogenous protein is a fusion protein and comprises amino acids encoded by the transgene and by the IL2RG and/or RAG (RAG1 or RAG2) gene. In some instances, the IL2RG and/or RAG (RAG1 or RAG2) sequences will be present on the amino (N)-terminal portion of the exogenous protein, while in others, the IL2RG and/or RAG (RAG1 or RAG2) sequences will be present on the carboxy (C)-terminal portion of the exogenous protein. In other instances, IL2RG and/or RAG (RAG1 or RAG2) sequences will be present on both the N- and C-terminal portions of the exogenous protein.

In some embodiments, the invention describes methods and compositions that can be used to express a transgene under the control of the IL2RG and/or RAG (RAG1 or RAG2) promoter in vivo. In some aspects, the transgene may encode a therapeutic protein of interest. The transgene may encode a protein such that the methods of the invention can be used for protein replacement. In some aspects, the transgene encodes an IL2RG or Rag (e.g., Rag1 or Rag2) protein that treats and/or prevents SCID or Omenn Syndrome. In other aspects, the transgene comprises a partial IL2RG and/or RAG (RAG1 or RAG2), gene sequence.

In some embodiments, the nuclease target and/or cleavage site is in an intron of the IL2RG and/or RAG (RAG1 or RAG2) gene such that a transgene (e.g., IL2RG-, Rag1 or Rag2-encoding transgene) is integrated into an intronic region of IL2RG and/or RAG (RAG1 or RAG2), for example into intron 1, intron 2 or intron 2, respectively. The transgene may be under the control of another endogenous or exogenous promoter of interest in vivo or in vitro, which exogenous promoter drives expression of the transgene (e.g., IL2RG-, Rag-encoding sequence). In preferred embodiments, the IL2RG, RAG1 or RAG2 transgene comprises a cDNA comprising exons 2 through 8 of IL2RG, exon 3 of RAG1, or exon 3 of RAG2, and further comprises a splice acceptor site such that upon integration and expression, the endogenous IL2RG exon 1, the endogenous RAG1 exon 1 or 2 or the endogenous RAG2 exon 1 or 2 sequences are linked to the transgenic exons 2-8 sequences, exon 3, or exon 3, respectively (depending on the RAG isoform) such that a wild type IL2RG, or Rag protein is produced and treats or prevents X-SCID or Omenn Syndrome.

In another aspect, a method of modifying an endogenous gene is described, the method comprising administering to the cell one or more polynucleotides encoding one or more nucleases (e.g., ZFNs, TALENs, TtAgo, CRISPR/Cas system) in the presence of one or more donor sequence encoding an IL2RG or Rag protein, such that the donor is integrated into the endogenous gene targeted by the nuclease. Integration of one or more donor molecule(s) occurs via homology-directed repair (HDR) or by non-homologous end joining (NHEJ) associated repair. In certain embodiments, one or more pairs of nucleases are employed, which nucleases may be encoded by the same or different nucleic acids. Any endogenous gene can be targeted for nuclease-mediated targeted integration of an IL2RG and/or RAG (RAG1 or RAG2) donor, including but not limited to IL2RG (e.g., intron 1), RAG1 (e.g. intron 1 or 2), RAG2 (e.g. intron 1 or 2), respectively, or a safe-harbor gene such as CCR5, AAVS1, Rosa26, ALB and/or HPRT.

In yet another aspect, provided herein is a cell comprising an IL2RG, RAG1 and/or RAG2 transgene which has been integrated into the genome in a targeted manner using a nuclease. In certain embodiments, the cell is made by the methods described herein. In other preferred embodiments, the IL2RG, RAG1 or RAG2 transgene is integrated into an intronic region of IL2RG (e.g., intron 1, including but not limited into a sequence as shown in any of SEQ ID NOs:47 to 60), RAG1 (e.g., intron 1 or 2, including but not limited into a sequences as shown as in any of SEQ ID Nos:81 to 83) or RAG2 (e.g., intron 1 or 2). In other embodiments, the IL2RG and/or RAG (RAG1 or RAG2) transgene is integrated into a safe-harbor locus, such as CCR5, AAVS1, ALB, Rosa26 and/or HPRT. The cells comprising the integrated IL2RG, and/or RAG (RAG1 or RAG2) transgene may express the transgene from an endogenous promoter (e.g., the IL2RG, RAG1 or RAG2 promoter, respectively) or, alternatively, the transgene may include regulatory and control elements such as exogenous promoters that drive expression of the IL2RG, RAG1 or RAG2 transgene (e.g., when integrated into a safe harbor locus). In certain embodiments, the cells comprising an IL2RG transgene do not include any viral vector sequences integrated into the genome.

In any of the methods and compositions described herein, the cells may be any eukaryotic cell. In certain embodiments, the cells are patient-derived, for example autologous CD34+ stem cells (e.g., mobilized in patients from the bone marrow into the peripheral blood via granulocyte colony-stimulating factor (GCSF) administration). The CD34+ cells can be harvested, purified, cultured, and the nucleases and/or IL2RG and/or RAG (RAG1 or RAG2) donor (e.g., an adenoviral vector donor) introduced into the cell by any suitable method.

In another aspect, the methods and compositions of the invention provide for the use of cells, cell lines and animals (e.g., transgenic animals) in the screening of drug libraries and/or other therapeutic compositions (i.e., antibodies, structural RNAs, etc.) for use in treatment of X-SCID or Omenn Syndrome. Such screens can begin at the cellular level with manipulated cell lines or primary cells, and can progress up to the level of treatment of a whole animal (e.g., human). Thus, in certain aspects, described herein is a method of treating and/or preventing X-SCID or Omenn Syndrome in a subject in need thereof, the method comprising administering one or more nucleases, polynucleotides and/or cells as described herein to the subject. In certain embodiments, a cell as described herein (e.g., a cell comprising an IL2RG, RAG1 or RAG2 transgene) is administered to the subject. In any of the methods described herein, the cell may be a stem cell derived from the subject (patient-derived stem cell).

In any of the compositions and methods described herein, the nucleases are introduced in mRNA form and/or using one or more non-viral or viral vector(s). In certain embodiments, the nuclease(s) are introduced in mRNA form. In other embodiments, the IL2RG and/or RAG (RAG1 or RAG2) transgene is introduced using a viral vector, for instance an adeno-associated vector (AAV) including AAV1, AAV3, AAV4, AAVS, AAV6, AAV8, AAV 8.2, AAV9, AAV rh10, AAV2/8, AAV2/5 and AAV2/6, or via a lentiviral or integration-defective lentiviral vector, and the nuclease(s) is(are) introduced in mRNA form. In still further embodiments, the nuclease(s) and donors are both introduced using one or more viral or non-viral vectors. The nuclease and donor may be carried on the same vector, on different vectors of the same type or on different vectors of different types. In certain embodiments, the nuclease(s) is(are) introduced in mRNA form (e.g., via electroporation) and the donor is introduced using an AAV (e.g., AAV2/6), lentivirus or integration defective lentivirus. In certain embodiments the donor is introduced as single-stranded DNA.

The nuclease(s) and donors may be introduced concurrently or in order. When introduced sequentially, any time period (e.g., seconds to hours) may elapse between administration of the nucleases and donors. In certain embodiments, the donors are introduced and after 12-36 hours (or any time therebetween), the nuclease are introduced into the cell. In certain embodiments, the modified cells are incubated for hours to days (or any time therebetween) and then are aliquoted and frozen.

The IL2RG and/or RAG (RAG1 or RAG2) donor may be delivered to any cell and integrated at any suitable gene. In certain embodiments, the endogenous gene is an IL2RG and/or RAG (RAG1 or RAG2) gene. In other embodiments, the nuclease targets a safe harbor gene such as HPRT, CCR5, AAVS1, Rosa26, ALB or the like. In certain embodiments, the IL2RG and/or RAG (RAG1 or RAG2) donor is integrated into an HPRT locus such that endogenous HPRT expression is inactivated and IL2RG and/or RAG (RAG1 or RAG2) is expressed from the HPRT locus (e.g., the donor includes control and regulatory elements necessary for expression). The resulting knockout of HPRT would allow for 6-thioguanine (6-TG) negative selection of cells not harboring the corrective IL2RG, RAG1 and/or RAG2 donor at the HPRT locus, for example in cases where levels of engraftment of CD34+ cells with the corrective IL2RG, RAG1 and/or RAG2 transgene cassette are low and/or if the initial level of modification of these cells is not sufficient.

Any cell can be modified using the compositions and methods of the invention, including but not limited to prokaryotic or eukaryotic cells such as bacterial, insect, yeast, fish, mammalian (including non-human mammals), and plant cells. In certain embodiments, the cell is an immune cell, for example a T-cell (e.g., CD4+, CD3+, CD8+, etc.), a dendritic cell, a B cell or the like. In other embodiments, the cell is a pluripotent, totipotent or multipotent stem cell, for example an induced pluripotent stem cell (iPSC), hematopoietic stem cells (e.g., CD34+), an embryonic stem cell or the like. In any of the methods or compositions described herein, the cell containing the IL2RG-encoding transgene can be a stem or progenitor cell. Specific stem cell types that may be used with the methods and compositions of the invention include embryonic stem cells (ESC), induced pluripotent stem cells (iPSC) and hematopoietic stem cells (e.g., CD34+ cells). The iPSCs can be derived from patient samples and from normal controls wherein the patient derived iPSC can be mutated to the normal or wild type gene sequence at the gene of interest, or normal cells can be altered to the known disease allele at the gene of interest. Similarly, the hematopoietic stem cells can be isolated from a patient (e.g., a SCID patient with a mutant form of one or more SCID-related genes such as IL2RG and/or Rag) or from a donor. These cells are then engineered to express functional SCID-related protein(s) such as IL2RG or Rag (e.g., Rag1 or Rag2), expanded and then reintroduced into the patient. In certain embodiments, the cell is a patient derived hematopoietic stem cell. In other embodiments, the cell is a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells.

A kit, comprising the nucleic acids, proteins and/or cells of the invention, is also provided. The kit may comprise nucleic acids encoding the nucleases, (e.g. RNA molecules or ZFN, TALEN, TtAgo or CRISPR/Cas system encoding genes contained in a suitable expression vector), or aliquots of the nuclease proteins, donor molecules, suitable stemness modifiers, cells, instructions for performing the methods of the invention, and the like.

These and other aspects will be readily apparent to the skilled artisan in light of disclosure as a whole.

BRIEF DESCRIPTION OF THE DRAWINGS

FIGS. 3A and 3B shows the result of a Surveyor™ nuclease digestion of PCR amplicons of the IL2RG locus after treatment of CD34+ HSPCs cells with the indicated ZFNs and TALENs. FIG. 3A shows activity results of exemplary ZFNs in gel format (percent indels indicated beneath each lane) and FIG. 3B is a table showing activity (indels) of the indicated pairs.

FIG. 4A depicts results with indicated ZFNs and TALENs. FIG. 4B shows results using the ZFN pair 44298/44271 (IL2RG specific ZFN, 4 μg). The left most bar of each group in each Figure shows colony forming units (erythroid) (CFU-E); the bar second from the left in each group shows burst forming erythroid units (BFU-E); the bar second from the right in each group shows colony forming units (granulocyte, monocyte) (CFU-GM); and the right most bar of each groups shows pluripotent colony forming units (granulocyte, erythrocyte, monocyte, megakaryocyte) (CFU-GEMM).

FIGS. 5A through 5D are schematics depicting the IL2RG gene with common mutations found in X-SCID patients (FIG. 5A); an exemplary donor with homology arms flanking the ZFN or TALEN cleavage site in intron 1, a 5' splice acceptor, and polyA tail to terminate transcription (FIG. 5B); and an exemplary intron 1 donor with a 2A-GFP construct to assay targeted integration and expression at the endogenous IL2RG locus via flow cytometry or other fluorescence detection assays (FIG. 5C). FIG. 5D is an illustration depicting the expression of a wild-type IL2RG protein following integration of the IL2RG exon 2-8 transgene donor into the endogenous IL2RG intron 1.

FIG. 6A shows IL2RG mRNA expression in the indicated cells. FIG. 6B depicts results of Miseq high-throughput DNA sequencing analysis and shows the percent modification in the indicated cells. "A" and "B" donors are identical except B contains a 3' Miseq primer binding sequence to assay TI by next generation sequencing. "Z" refers to ZFNs, "T" refers to TALENs, and "N" refers to naïve cells.

FIG. 7A shows results from cells harvested 3 days post nucleofection; FIG. 7B shows results from cells harvested 10 days post nucleofection.

FIG. 8A shows results from cells harvested 3 days post nucleofection; FIG. 8B shows results from cells harvested 10 days post nucleofection.

FIG. 9A shows results from K562 cells; FIG. 9B shows results from CD34+ HSPCs.

FIG. 10A shows results from K562 cells; FIG. 9B shows results from CD34+ HSPCs FIG. 11A is a gel showing PCR using primers targeting outside the region of homology of the donor, thus generating both wild-type and TI (larger) products. A donor-specific restriction enzyme fragmented the larger molecular weight product (right part of the gel), indicating it was indeed the correct TI product. The percentage of indels ("% indels) (insertions and/or deletions following nuclease cleavage) listed are from parallel high-throughput DNA sequencing analysis. FIG. 11B shows PCR amplification of the same set of samples using either ethidium bromide (left, 30 cycles of PCR) or the incorporation of radioactive nucleotides (right, 23 cycles of PCR) to detect the DNA. Use of fewer PCR cycles prevents formation of heteroduplex DNA between different alleles of IL2RG and gives a superior signal to noise ratio for detection of targeted integration. Levels of TI ("% TI") are shown below % indels.

FIGS. 13A and 13B are graphs depicting methylcellulose assay and high-throughput DNA sequencing analysis of individual CD34-derived cell clones. FIG. 13A shows number of colonies formed following treatment with the ZFN pair 44271/44298 delivered as mRNA, IL2RG partial cDNA donor delivered with AAV6, or both. GFP mRNA was delivered as a control. The left most bar of each group shows colony forming units (erythroid) (CFU-E); the bar second from the left in each group shows burst forming erythroid units (BFU-E); the bar second from the right in each group shows colony forming units (granulocyte, monocyte) (CFU-GM); and the right most bar of each groups shows pluripotent colony forming units (granulocyte, erythrocyte, monocyte, megakaryocyte) (CFU-GEMM). FIG. 13B shows the percent of modified alleles (targeted integration shown in white portions of the bars, indels following NHEJ shown in shaded at the bottom of each bar) under the indicated conditions.

FIG. 14A shows the percent of viable cells before and after cryopreservation under the indicated conditions. The left most bar in each group shows percent viability at day 0 before thawing; the middle bar shows percent viability at day 0 post-thawing; and the right most bar in each group shows the percent viability at day 3 post-thawing. FIG. 14B shows the percent of modified alleles (targeted integration shown in white portions of the bars at the top of the bars, indels following NHEJ shown in shaded at the bottom of each bar) under the indicated conditions. The percent of TI detected is indicated by white boxes. In some samples, (ZFNs, Day 0 Prethaw; GFP—Day 3 Post Thaw; and ZFNs—Day 3 Post Thaw), the signal represented by white boxes is very low such that the boxes are compressed to a black line.

FIG. 15A depicts the RAG1 gene were the gene comprises three exons and two introns, where variable splicing results in two isoforms, either exon 1 linked to exon 3 (isoform 1) or exon 2 linked to exon 3 (isoform 2). The sequences encoding the Rag1 polypeptide are found in exon 3. FIG. 15B depicts the RAG2 gene which also comprises three exons and two introns. Variable splicing also results in two isoforms, either exon 1 linked to exon 3 (isoform 1) or exon 1 linked to exon 2 and exon 3 (isoform 3).

FIGS. 16A and 16B are schematics depicting the method used to correct RAG1 gene mutations. FIG. 16A shows an exemplary donor with homology arms flanking the ZFN cleavage site in intron 2, a 5' splice acceptor, and polyA tail to terminate transcription. Also shown are the locations of the two ZFN target sites in intron 2. FIG. 16B is an illustration depicting the splicing of a wild-type RAG1 transcript for the two RAG1 isoforms following integration of the RAG1 cDNA transgene donor into the endogenous RAG1 intron 2.

FIG. 17A depicts the qPCR scheme of discriminating between the wild-type and the codon-optimized corrective cDNA transgene for RAG1 isoform 1. FIG. 17B shows the percentage of exogenous codon-optimized RAG1 transcripts relative to wild-type RAG1 transcripts. FIG. 17C shows Miseq analysis of these same samples and indicates ~5% targeted integration of the corrective RAG1 transgene yields ~6% total levels of correct, fully maturely spliced RAG1 transcripts. The ZFN pair used in these experiments was the Site 4 specific ZFN pair 50773/49812.

FIGS. 18A and 18B depict targeted integration of an exemplary corrective RAG1 cDNA donor in CD34+ cells using BTX electroporation. FIG. 18A shows results with cryopreserved cells modified with either the "Site 1" ZFN pair (50698/50718). FIG. 18B shows results using the "Site 4" ZFN pair (50773/49812) delivered as mRNA and a corrective RAG1 cDNA donor delivered with AAV6. Data shown is from 1 day post transfection ("1DPT").

FIG. 19A shows the percent of viable cells before cryopreservation under the indicated conditions. FIG. 19B shows the percent of modified alleles under the indicated conditions. The percent of TI detected is indicated by grey boxes.

DETAILED DESCRIPTION

Figure 1:
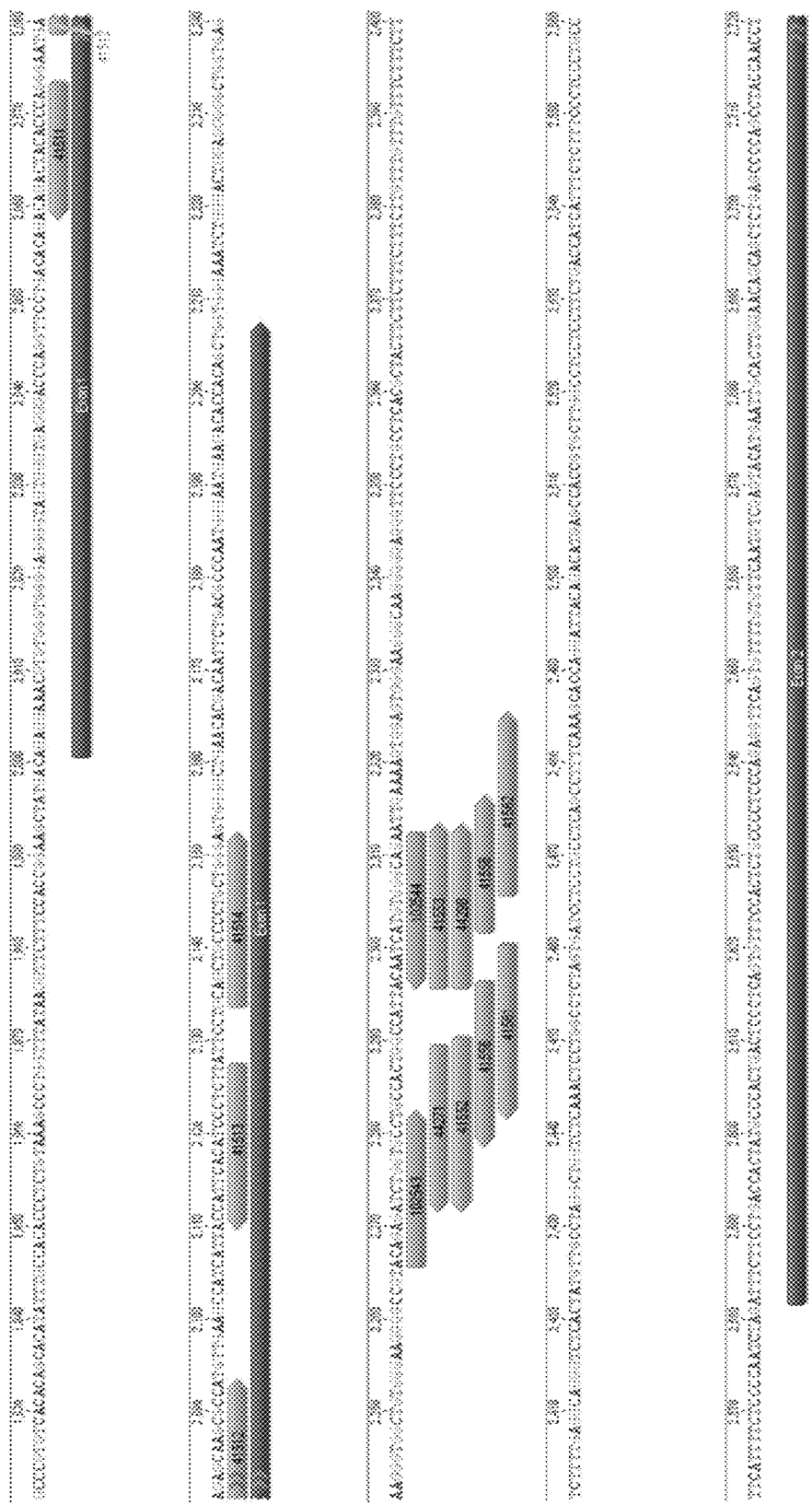
FIG. 1 (SEQ ID NO:101) is a schematic representation of the IL2RG-specific nuclease target sites in Exon 1 and Intron 1 of the endogenous IL2RG gene. Darker grey bars indicate Exons 1 and 2, while the shorter light grey bars indicate the target sites for the nucleases.

Disclosed herein are compositions and methods for targeted integration of a corrective SCID-related protein (e.g., IL2RG, RAG1 or RAG2) transgene into a cell (e.g., lymphocyte precursors such as CD34+ hematopoietic stem cells). The cells are suitable for infusion into severe combined immunodeficiency (X-SCID or SCID) patients such that subsequent in vivo differentiation of these precursors into cells expressing the functional proteins lacking or deficient in the subject with a SCID disorder is provided by the cell, which cells can treat and/or prevent disease in the recipient SCID patient. Cells comprising an IL2RG transgene are suitable for infusion into X-SCID patients such that subsequent in vivo differentiation of these stem cells into cells that express the functional IL2RG protein treat and/or prevent X-SCID disease in the patient. Similarly, stem cells comprising the RAG1 or RAG2 transgenes are suitable for infusion into Omenn Syndrome patients such that subsequent in vivo differentiation of these precursors into cells expression the functional Rag1 and/or Rag2 proteins treats and/or prevents disease in an Omenn Syndrome patient.

Targeted integration of IL2RG, RAG1 or RAG2 (e.g., into intronic regions of IL2RG, RAG1 and/or RAG2 and/or a safe harbor gene) avoids the issues associated with gene therapy methods that involve random integration of IL2RG, RAG1 or RAG2 into the genome as well as methods that involve integration into exons of IL2RG, RAG1 or RAG2. In particular, random integration often results in adverse events due to the partially transcribed upstream region of the locus and, in addition, intronic insertion at the IL2RG, RAG1 or RAG2 locus utilizes the endogenous transcriptional regulatory elements such as native RNA splicing, promoters, and enhancers which least invasively replaces the defective locus with a correct form.

The invention contemplates the integration of a donor comprising any functional IL2RG or Rag protein, including a functional fragment of these proteins such as a partial cDNA comprising exons 2-8 of the IL2RG gene, a splice acceptor sequence and a polyadenylation sequence. Also contemplated is the integration of a donor comprising a full cDNA comprising exon 3 of RAG1 or RAG2, a splice acceptor sequence and a polyadenylation sequence. Targeted integration of the IL2RG donor into intron 1 of the endogenous IL2RG will result in the expression of a wild-type IL2RG or common gamma protein, thus treating or preventing X-SCID. Targeted integration of the RAG1 or RAG2 donor into intron 2 of the endogenous RAG1 or RAG 2 gene, respectively, will result in the expression of wild type Rag1 or Rag2, thus treating or preventing Omenn Syndrome.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,586,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, TALENs, TtAgo or CRISPR/Cas systems can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 8,623,618; 7,888,121; 7,914,796; and 8,034,598 and U.S. Publication No. 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™) Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE, TtAgo or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE, TtAgo or Cas DNA-binding domain is fused to an activation domain, the ZFP, TALE, TtAgo or Cas DNA-binding domain and the activation domain are in operative linkage if, in the fusion polypeptide, the ZFP, TALE, TtAgo or Cas DNA-binding domain portion is able to bind its target site and/or its binding site, while the activation domain is able to upregulate gene expression. When a fusion polypeptide in which a ZFP, TALE, TtAgo or Cas DNA-binding domain is fused to a cleavage domain, the ZFP, TALE, TtAgo or Cas DNA-binding domain and the cleavage domain are in operative linkage if, in the fusion polypeptide, the ZFP, TALE, TtAgo or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a disorder.

"Stemness" refers to the relative ability of any cell to act in a stem cell-like manner, i.e., the degree of toti-, pluri-, or oligopotentcy and expanded or indefinite self-renewal that any particular stem cell may have.

Fusion Molecules

Described herein are compositions, for example nucleases, that are useful for cleavage of a selected target gene (e.g., IL2RG) in a cell. In certain embodiments, one or more components of the fusion molecules (e.g., nucleases) are naturally occurring. In other embodiments, one or more of the components of the fusion molecules (e.g., nucleases) are non-naturally occurring, i.e., engineered in the DNA-binding molecules and/or cleavage domain(s). For example, the DNA-binding portion of a naturally-occurring nuclease may be altered to bind to a selected target site (e.g., a single guide RNA of a CRISPR/Cas system or a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Molecules

The fusion molecules described herein can include any DNA-binding molecule (also referred to as DNA-binding domain), including protein domains and/or polynucleotide DNA-binding domains.

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" disclosed as SEQ ID NO:96), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) Science 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibicl). Engineered TAL proteins have been linked to a FokI cleavage half domain to yield a TAL effector domain nuclease fusion (TALEN). See, e.g., U.S. Pat. No. 8,586,526; Christian et al ((2010)<*Genetics* epub 10.1534/genetics.110.120717). In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some aspects, the DNA-binding domain targets an IL2RG or RAG gene. In certain embodiments, the DNA-binding domain targets an intronic region of IL2RG or a RAG gene, for example intron 1 or intron 2.

Selection of target sites (e.g., within an intronic region of IL2RG or a RAG gene); ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding molecule is part of a CRISPR/Cas nuclease system. See, e.g., U.S. Pat. No. 8,697,359 and U.S. Patent Publication No. 20150056705. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al (2015) *Nature* 510, p. 186).

In some embodiments, the DNA binding molecule is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celcius. Ago-RNA-mediated DNA cleavage could be used to effect a panopoly of outcomes including gene knock-out, targeted gene addition, gene correction, targeted gene deletion using techniques standard in the art for exploitation of DNA breaks.

Thus, the nuclease comprises a DNA-binding molecule in that specifically binds to a target site in any gene into which it is desired to insert a donor (transgene), particularly an IL2RG and/or Rag transgene.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity, including for use in genome modification in a variety of organisms. See, for example, U.S. Pat. Nos. 7,888,121; 8,623,618; 7,888,121; 7,914,796; and 8,034,598 and U.S. Publication No. 20110201055. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., Si Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,623,618; 7,888,121; 7,914,796; and 8,034,598 and U.S. Publication No. 20110201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Cleavage domains with more than one mutation may be used, for example mutations at positions 490 (E→K) and 538 (I→K) in one cleavage half-domain to produce an engineered cleavage half-domain designated "E490K: I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey'" mutations (see Guo et al, (2010) *J. Mol. Biol.* 400(1):96-107).

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA-binding domains can be engineered to bind to any sequence of choice. An engineered DNA-binding domain can have a novel binding specificity, compared to a naturally-occurring DNA-binding domain.

In certain embodiments, the nuclease(s) target(s) an IL2R2 gene or RAG gene (e.g., RAG1 or RAG2), for example an intron (e.g., intron 1 or intron 2) or an exon (e.g., exon 1) of the gene.

In certain embodiments, the nuclease target(s) a "safe harbor" loci such as the AAVS1, HPRT, ALB and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

Addition non-limiting examples of suitable target genes include a beta (β) globin gene (HBB), a gamma (δ) globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, a Rag-1 gene, an RFXS gene, a FAD2 gene, a FAD3 gene, a ZP15 gene, a KASII gene, a MDH gene, and/or an EPSPS gene. In some aspects, the nuclease(s) binds to and/or cleaves a check point inhibitor gene, for example PD-1, CTLA4, receptors for the B7 family of inhibitory ligands, or cleaves a receptor or ligand gene involved in signaling through LAG3, 2B4, BTLA, TIM3, A2aR, and killer inhibitor receptors (KIRs and C-type lectin receptors), see Pardoll (2012) *Nat Rev Cancer* 12(4):252, an HLA complex gene (class I: HLA-A, HLA-B, HLA-C, HLA-E, HLA-F, HLA-G, B2M; class II: HLA-DMA, HLA-DOA, HLA-DPA1, HLA-DQA, HLA-DRA, HLA-DMB, HLA-DOB, HLA-DPB1, HLA-DQB, HLA-DRB) or TCR; and/or a gene encoding a product involved in the peptide loading process and antigen processing for the HLA complexes (e.g. TAP, tapasin, calreticulin, calnexin, LMP2, LMP7 or Erp57). See, e.g., U.S. Pat. Nos. 8,956,828 and 8,945,868.

Donors

In certain embodiments, the present disclosure relates to nuclease-mediated targeted integration of an exogenous sequence encoding an IL2RG and/or Rag protein (e.g., any functional fragment of an IL2RG and/or Rag protein) into the genome of a cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence (e.g., a transgene) flanked by two regions of homology to allow for efficient HDR at the location of interest or can be integrated via non-homology directed repair mechanisms. See, e.g., U.S. Pat. Nos. 9,045,763; 9,005,973 and 7,888,121. Additionally, donor sequences can comprise a vector molecule containing sequences that are not homologous to the region of interest in cellular chromatin. A donor molecule can contain several, discontinuous regions of homology to cellular DNA. Further, for targeted insertion of sequences not normally present in a region of interest, said sequences can be present in a donor nucleic acid molecule and flanked by regions of homology to sequence in the region of interest.

As with nucleases, the donors can be introduced into any form. In certain embodiments, the donors may be introduced using DNA and/or viral vectors by methods known in the art. See, e.g., U.S. Pat. Nos. 9,005,973; 8,936,936 and 8,703,489. The donor may be introduced into the cell in double- or single-stranded form. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In some embodiments, the SCID-related (e.g., IL2RG and/or RAG) transgene is integrated into the endogenous locus of the gene to correct a mutant version (e.g., in a cell from a SCID patient that is lacking or deficient in a functional version of the SCID-related gene). In certain embodiments, an IL2RG transgene is integrated into an endogenous IL2RG gene, for example an intronic region (e.g., intron 1) of a mutant IL2RG associated with X-SCID. In certain embodiments, a RAG transgene (e.g., RAG1 or RAG2) is integrated into an endogenous RAG gene, for example an intronic region (e.g., intron 1 or 2 of RAG1 and/or RAG2) of a mutant RAG associated with a form of SCID such as Omenn Syndrome. The donor may include any SCID-related protein-encoding sequences that produce a functional protein, including but not limited to full-length SCID-related genes (e.g., IL2RG, RAG1, and/or RAG2), partial (functional) sequences of SCID-related genes (e.g., exons 2-8 of IL2RG, exon 3 of RAG1 or RAG2, etc.) and combinations thereof. In other embodiments, the SCID-related gene transgene is integrated into any endogenous locus, for example a safe-harbor locus. See, e.g., U.S. Pat. Nos. 7,951,925; 8,110,379; and U.S. Patent Publication Nos. 2010218264; 20130177983 and 20130196373.

Furthermore, although not required for expression, exogenous sequences may also include transcriptional or translational regulatory or other sequences, for example, promoters, enhancers, insulators, internal ribosome entry sites, sequences encoding 2A peptides and/or polyadenylation signals. Additionally, splice acceptor sequences may be included. Exemplary splice acceptor site sequences are known to those of skill in the art and include, by way of example only, CTGACCTCTTCTCTTCCTCCCACAG, (SEQ ID NO:1) (from the human HBB gene) and TTTCTCTCCACAG (SEQ ID NO:2) (from the human Immunoglobulin-gamma gene).

The SCID-related transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear or chimeric antigen receptors (CARs)), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the transgene may include, for example, wild-type genes to replace mutated endogenous sequences. For example, a wild-type (or other functional) IL2RG and/or RAG gene sequence may be inserted into the genome of a stem cell in which the endogenous copy of the gene is mutated. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Cells

Thus, provided herein are genetically modified cells comprising a SCID-related transgene, namely a transgene that expresses a functional protein lacking or deficient in a SCID in the cell, including cells produced by the methods described herein. The transgene is integrated in a targeted manner into the cell's genome using one or more nucleases. In certain embodiments, the transgene is integrated into IL2RG, for example a mutant IL2RG gene as found in X-SCID patients. In certain embodiments, the transgene is integrated into a RAG gene, for example a mutant RAG1 and/or RAG2 gene as found in Omenn Syndrome patients. The transgene may be integrated into any intronic or exonic region of IL2RG or a RAG gene, for example intron 1 or intron 2. In other embodiments, the transgene is integrated into a safe harbor gene. Thus, provided herein are genetically modified cells comprising a SCID-related transgene (that expresses a functional protein lacking or deficient in a SCID) integrated in intron 1 or intron 2 of a SCID-related gene as well as cells descended from these cells that include the genetic modification.

Unlike random integration, targeted integration ensures that the transgene is integrated into a specified gene. The transgene may be integrated anywhere in the target gene. In certain embodiments, the transgene is integrated at or near the nuclease cleavage site, for example, within 1-300 (or any value therebetwen) base pairs upstream or downstream of the site of cleavage, more preferably within 1-100 base pairs (or any value therebetween) of either side of the cleavage site, even more preferably within 1 to 50 base pairs (or any value therebetween) of either side of the cleavage site. In certain embodiments, the integrated sequence comprising the transgene does not include any vector sequences (e.g., viral vector sequences).

Any cell type can be genetically modified as described herein to comprise an IL2RG transgene, including but not limited to cells and cell lines. Other non-limiting examples of IL2RG-transgene containing cells as described herein include T-cells (e.g., CD4+, CD3+, CD8+, etc.); dendritic cells; B-cells; autologous (e.g., patient-derived) or heterologous pluripotent, totipotent or multipotent stem cells (e.g., CD34+ cells, induced pluripotent stem cells (iPSCs), embryonic stem cells or the like). In certain embodiments, the cells as described herein are CD34+ cells derived from an X-SCID patient.

The SCID-related protein-expressing cells as described herein are useful in treating and/or preventing SCID (e.g., X-SCID and/or Omenn Syndrome) in a subject with the disorder, for example, by ex vivo therapies. The nuclease-modified cells can be expanded and then reintroduced into the patient using standard techniques. See, e.g., Tebas et al (2014) *New Eng J Med* 370(10):901. In the case of stem cells, after infusion into the subject, in vivo differentiation of these precursors into cells expressing the functional IL2RG protein also occurs. Pharmaceutical compositions comprising the cells as described herein are also provided. In addition, the cells may be cryopreserved prior to administration to a patient.

The cells and ex vivo methods as described herein provide treatment and/or prevention of SCID in a subject and eliminate the need for continuous prophylactic pharmaceutical administration or risky procedures such as allogeneic bone marrow transplants or gamma retroviral delivery. As such, the invention described herein provides a safer, cost-effective and time efficient way of treating and/or preventing SCID.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to SCID patients.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824, and U.S. Patent Publication No. 20140335063, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357: 455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, lipid nanoparticles (LNP), naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc. (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. In some aspects, the nucleases are delivered as mRNAs and the transgene is delivered via other modalities such as viral vectors, minicircle DNA, plasmid DNA, single-stranded DNA, linear DNA, liposomes, nanoparticles and the like.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989). Any AAV serotype can be used, including AAV1, AAV3, AAV4, AAV5, AAV6 and AAV5, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., Infection 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, sublingual or intracranial infusion) topical application, as described below, or via pulmonary inhalation. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application, inhalation and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) Proc. Natl. Acad. Sci. USA 93:11382-11388; Dull et al. (1998) J. Virol. 72:8463-8471; Zuffery et al. (1998) J. Virol. 72:9873-9880; Follenzi et al. (2000) Nature Genetics 25:217-222; U.S. Pat. No. 8,936,936.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. Multiple vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are for providing therapies for SCID, for example via the provision of proteins lacking or deficient in a SCID disorder. The cell may be modified in vivo or may be modified ex vivo and subsequently administered to a subject. Thus, the methods and compositions provide for the treatment and/or prevention of a SCID disorder.

Targeted integration of an SCID-related transgene (e.g., IL2RG and/or RAG transgene) may be used to correct an aberrant SCID-related gene, insert a wild type gene, or change the expression of an endogenous gene. For instance, a wild-type transgene encoding IL2RG, which is deficient in X-SCID patients, may be integrated into a cell to provide a cell that produces a functional protein. Similarly, a wild-type transgene encoding a RAG gene (e.g., RAG1 or RAG2), which is deficient in Omenn Syndrome SCID patients, may be integrated into a cell to provide a cell that produces a functional Rag protein. Genomic editing may also include correction of mutations (e.g., point mutations) in a faulty endogenous gene, thereby resorting expression of the gene and treating the disorder.

By way of non-limiting example, the methods and compositions described herein can be used for treatment and/or prevention of SCID.

The following Examples relate to exemplary embodiments of the present disclosure in which the nuclease comprises a zinc finger nuclease (ZFN) or TALEN. It will be appreciated that this is for purposes of exemplification only and that other nucleases can be used, for example TtAgo and CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins.

EXAMPLES

Example 1: Zinc Finger Protein Nucleases (ZFN) and TALE-Nucleases (TALENs) and Guide RNAs Targeted to IL2RG or RAG Zinc finger proteins targeted to IL2RG or RAG1 were designed and incorporated into mRNA, plasmids, AAV or adenoviral vectors essentially as described in Urnov et al. (2005) Nature 435(7042):646-651, Perez et al (2008) Nature Biotechnology 26(7):808-816, and as described in U.S. Pat. No. 6,534,261. Table 1 shows the recognition helices within the DNA binding domain of exemplary IL2RG or RAG1 ZFPs while Table 2 shows the target sites for these ZFPs (DNA target sites indicated in uppercase letters; non-contacted nucleotides indicated in lowercase). Nucleotides in the target site that are contacted by the ZFP recognition helices are indicated in uppercase letters; non-contacted nucleotides indicated in lowercase.

TABLE 1

Zinc finger proteins recognition helix designs

| SBS # | F1 | F2 | F3 | F4 | F5 | F6 |
|---|---|---|---|---|---|---|
| IL2RG-specific designs | | | | | | |
| 41511 | WRSCRSA (SEQ ID NO: 3) | DRSALSR (SEQ ID NO: 4) | QSGSLTR (SEQ ID NO: 5) | DRSHLTR (SEQ ID NO: 6) | RLDWLPM (SEQ ID NO: 7) | NA |

TABLE 1-continued

Zinc finger proteins recognition helix designs

Design

| SBS # | F1 | F2 | F3 | F4 | F5 | F6 |
|---|---|---|---|---|---|---|
| 41512 | QSGDLTR (SEQ ID NO: 8) | RRADLSR (SEQ ID NO: 9) | QRSNLDS (SEQ ID NO: 10) | RSANLAR (SEQ ID NO: 11) | QSANRTK (SEQ ID NO: 12) | NA |
| 41513 | LRHHLTR (SEQ ID NO: 13) | LRHNLRA (SEQ ID NO: 14) | RSDALSR (SEQ ID NO: 15) | TSGNLTR (SEQ ID NO: 16) | RSDHLSA (SEQ ID NO: 17) | ESRYLMV (SEQ ID NO: 18) |
| 41514 | QSGHLAR (SEQ ID NO: 19) | RKWTLQG (SEQ ID NO: 20) | RSDDLTR (SEQ ID NO: 21) | DRSTRRQ (SEQ ID NO: 22) | QSSDLSR (SEQ ID NO: 23) | QSGDLTR (SEQ ID NO: 8) |
| 41552 | TSGNLTR (SEQ ID NO: 16) | QSNDLNS (SEQ ID NO: 24) | DRSHLTR (SEQ ID NO: 6) | QSGDLTR (SEQ ID NO: 8) | RSDSLLR (SEQ ID NO: 25) | QSYDRFQ (SEQ ID NO: 26) |
| 41553 | QSGNLAR (SEQ ID NO: 27) | QSGDLTR (SEQ ID NO: 8) | RSDHLST (SEQ ID NO: 28) | RSDARTT (SEQ ID NO: 29) | DRSTRIT (SEQ ID NO: 30) | QNATRIN (SEQ ID NO: 31) |
| 41556 | DRSHLTR (SEQ ID NO: 6) | QSGDLTR (SEQ ID NO: 8) | RSDSLLR (SEQ ID NO: 25) | QSYDRFQ (SEQ ID NO: 26) | RSDHLST (SEQ ID NO: 28) | QSANRTK (SEQ ID NO: 12) |
| 41558 | RMYTLSK (SEQ ID NO: 32) | QSGNLAR (SEQ ID NO: 27) | QSGDLTR (SEQ ID NO: 8) | RSDHLST (SEQ ID NO: 28) | RSDARTT (SEQ ID NO: 29) | NA |
| 41561 | QSGDLTR (SEQ ID NO: 8) | RSDALAR (SEQ ID NO: 33) | ERGTLAR (SEQ ID NO: 34) | RSDALTQ (SEQ ID NO: 35) | QSGALAR (SEQ ID NO: 36) | HKSARAA (SEQ ID NO: 37) |
| 41562 | QSGHLAR (SEQ ID NO: 19) | LLHHLNN (SEQ ID NO: 38) | QSGNLAR (SEQ ID NO: 27) | WRISLAA (SEQ ID NO: 39) | RSDNLSA (SEQ ID NO: 40) | RSQNRTR (SEQ ID NO: 41) |
| 44271 | TSGNLTR (SEQ ID NO: 16) | QSNDLNS (SEQ ID NO: 24) | YQGVLTR (SEQ ID NO: 42) | RSDNLRE (SEQ ID NO: 43) | RSDHLSQ (SEQ ID NO: 44) | TSANRTT (SEQ ID NO: 45) |
| 44298 | QSGNLAR (SEQ ID NO: 27) | QSGDLTR (SEQ ID NO: 8) | RSDHLSQ (SEQ ID NO: 44) | QSNGLTQ (SEQ ID NO: 46) | DRSTRIT (SEQ ID NO: 30) | QNATRIN (SEQ ID NO: 31) |

RAG1-specific designs

| SBS # | F1 | F2 | F3 | F4 | F5 | F6 |
|---|---|---|---|---|---|---|
| 54972 | QRSNLVR (SEQ ID NO: 61) | TSGSLTR (SEQ ID NO: 62) | QGCNLGK (SEQ ID NO: 63) | DRSNLTR (SEQ ID NO: 64) | QSGDLTR (SEQ ID NO: 8) | WSTSLRA (SEQ ID NO: 65) |
| 50698 | RSDSLLR (SEQ ID NO: 25) | WLSSLSA (SEQ ID NO: 66) | DRSNLSR (SEQ ID NO: 67) | HRQHLVT (SEQ ID NO: 68) | LRHHLTR (SEQ ID NO: 13) | DRSTLRQ (SEQ ID NO: 69) |
| 50718 | QSSNLAR (SEQ ID NO: 70) | TSGSLTR (SEQ ID NO: 62) | QGCNLVK (SEQ ID NO: 71) | DRSNLTR (SEQ ID NO: 64) | QSGDLTR (SEQ ID NO: 8) | WSTSLRA (SEQ ID NO: 65) |
| 54950 | RSDSLLR (SEQ ID NO: 25) | LRQNLVA (SEQ ID NO: 72) | DRSNLSR (SEQ ID NO: 67) | HRQHLVT (SEQ ID NO: 68) | HRHHLGQ (SEQ ID NO: 73) | QNATRTK (SEQ ID NO: 74) |
| 55002 | QSGNLAR (SEQ ID NO: 27) | RHWSLSV (SEQ ID NO: 75) | QRTNLVE (SEQ ID NO: 76) | ASKTRTN (SEQ ID NO: 77) | RSDVLST (SEQ ID NO: 78) | STAALSY (SEQ ID NO: 79) |
| 50773 | NPANLTR (SEQ ID NO: 97) | QNATRTK (SEQ ID NO: 74) | QSSDLSR (SEQ ID NO: 23) | QLANLQT (SEQ ID NO: 80) | TSGNLTR (SEQ ID NO: 16) | N/A |
| 55005 | QSGNLAR (SEQ ID NO: 27) | RHWSLSV (SEQ ID NO: 75) | QRTNLVE (SEQ ID NO: 76) | ASKTRTN (SEQ ID NO: 77) | RSDVLST (SEQ ID NO: 78) | STAALSY (SEQ ID NO: 79) |
| 49812 | QSGNLAR (SEQ ID NO: 27) | RHWSLSV (SEQ ID NO: 75) | QRTNLVE (SEQ ID NO: 76) | ASKTRTN (SEQ ID NO: 77) | RSDVLST (SEQ ID NO: 78) | STAALSY (SEQ ID NO: 79) |

TABLE 2

Target Sites of zinc finger proteins

| SBS # | Target site |
|---|---|
| IL2RG-specific target sites | |
| 41511 | ccCTGGGTGTAGTCTGTctgtgtcagga (SEQ ID NO: 47) |
| 41512 | atGAAGAGCAAGCGCCAtgttgaagcca (SEQ ID NO: 48) |
| 41513 | atAAGAGGGATGTGAATGGTaatgatgg (SEQ ID NO: 49) |
| 41514 | ctGCAGCTgCCCCTGCTGGGAgtggggc (SEQ ID NO: 50) |
| 41552 | ggCCAGTGGCAGGCaCCAGATctctgta (SEQ ID NO: 51) |
| 41553 | ttACAATCATGTGGGCAGAAttgaaaag (SEQ ID NO: 52) |
| 41556 | tgTAATGGCCAGTGGCAGGCaccagatc (SEQ ID NO: 53) |
| 41558 | tcATGTGGGCAGAATTGaaaagtggagt (SEQ ID NO: 54) |
| 41561 | tgATTGTAATGGCCaGTGGCAggcacca (SEQ ID NO: 55) |
| 41562 | gtGGGCAGaATTGAAaAGTGGAgtggga (SEQ ID NO: 56) |
| 44271 | gcCAGTGGCAGGCACCAGATctctgtac (SEQ ID NO: 57) |
| 44298 | ttACAATCATGTGGGCAGAAttgaaaag (SEQ ID NO: 58) |
| RAG1-specific target sites | |
| 54972 | tgTGTACAGACTAAGTTGAAgatgttan (SEQ ID NO: 81) |
| 50698 | ttCCAAGTAATAACTGTGTGctcaagtg (SEQ ID NO: 82) |
| 50718 | tgTGTACAGACTAAGTTGAAgatgttan (SEQ ID NO: 81) |
| 54950 | ttCCAAGTAATAACTGTGTGctcaagtg (SEQ ID NO: 82) |
| 55002 | ctTTTATGACCCATTTGGAAgaaataaa (SEQ ID NO: 83) |
| 50773 | atGATAAAGCTGCAAACccaaagaaact (SEQ ID NO: 84) |
| 55005 | ctTTTATGACCCATTTGGAAgaaataaa (SEQ ID NO: 83) |
| 49812 | ctTTTATGACCCATTTGGAAgaaataaa (SEQ ID NO: 83) |

All ZFN pairs were tested for cleavage activity and found to be active. Note that RAG1-specific ZFNs 55002, 55005 and 49812 all comprise the same zinc finger helices, but have different linkers between zinc finger helix 4 and 5 contained within the DNA binding protein. ZFN 55002 comprises a TGEKP linker (SEQ ID NO:98), 55005 comprises a TGERG linker (SEQ ID NO:99) and 49812 comprises a TGSQKP linker.

TALENs targeted to IL2RG were designed and incorporated into mRNA, plasmids, AAV or adenoviral vectors essentially as described in U.S. Pat. No. 8,586,526, including N-cap and/or C-cap sequences. The RVDs and target sites of the indicated exemplary TALENs are shown below in Tables 3 and 4.

TABLE 3

IL2RG-specific TALE RVDs

| SBS # | RVDs |
|---|---|
| 102543 | NI-HD-NI-NN-NI-NN-NI NG HD NG NN NN NG NN HD HD NG |
| 102544 | NG HD NG NN HD HD HD NI-HD-NI-NG-NN-NI-NG-NG-NN-NG |

TABLE 4

IL2RG-specific TALE Target Sites

| SBS # | Target site |
|---|---|
| 102543 | gtACAGAGATCTGGTGCCTgc (SEQ ID NO: 59) |
| 102544 | atTCTGCCCACATGATTGTaa (SEQ ID NO: 60) |

Specific CRISPR/Cas nucleases and guide RNAs are designed using methods in the art. See e.g. U.S. Patent Publication No. 20150056705. Table 5 shows exemplary guide RNAs (gRNAs) for use with *S. pyogenes* Cas9 for targeting intron 1 of IL2RG, and introns 1 and 2 for RAG1 and RAG2. Sequences corresponding to the PAM sequence are shown in bold, and the location of the targeted sequence is shown as corresponds to the UCSC GRCh37/hg19 human genome assembly.

The nucleases (ZFNs, CRISPR/Cas systems and TALENs) can include engineered cleavage domains, in particular the heterodimers disclosed in U.S. Pat. No. 8,623,618 (e.g., ELD and KKR engineered cleavage domains).

Example 2: Activity of IL2RG-Targeted Nucleases

ZFNs and TALENs targeting intron 1 and exon 1 of the IL2RG gene (see FIG. 1) were used to test the ability of these nucleases to cleave (e.g., induce DSBs) at a specific target site. In particular, the Cel-I mismatch assay (Surveyor™, Transgenomics; Perez et al, (2008) *Nat. Biotechnol.* 26: 808-816 and Guschin et al, (2010) *Methods Mol Biol.* 649:247-56) was used where PCR-amplification of the target site was followed by quantification of insertions and deletions (indels) using the mismatch detecting enzyme Cel-I (Yang et al, (2000) *Biochemistry* 39, 3533-3541) which provides a lower-limit estimate of DSB frequency. After introduction of the polynucleotides at standard conditions (37° C.) or cold-shock conditions (30° C.) (see, e.g., U.S. Pat. No. 8,772,008) into human K562 cells or CD34+ cells genomic DNA was isolated from the cells using the DNeasy™ kit (Qiagen).

Figure 2:
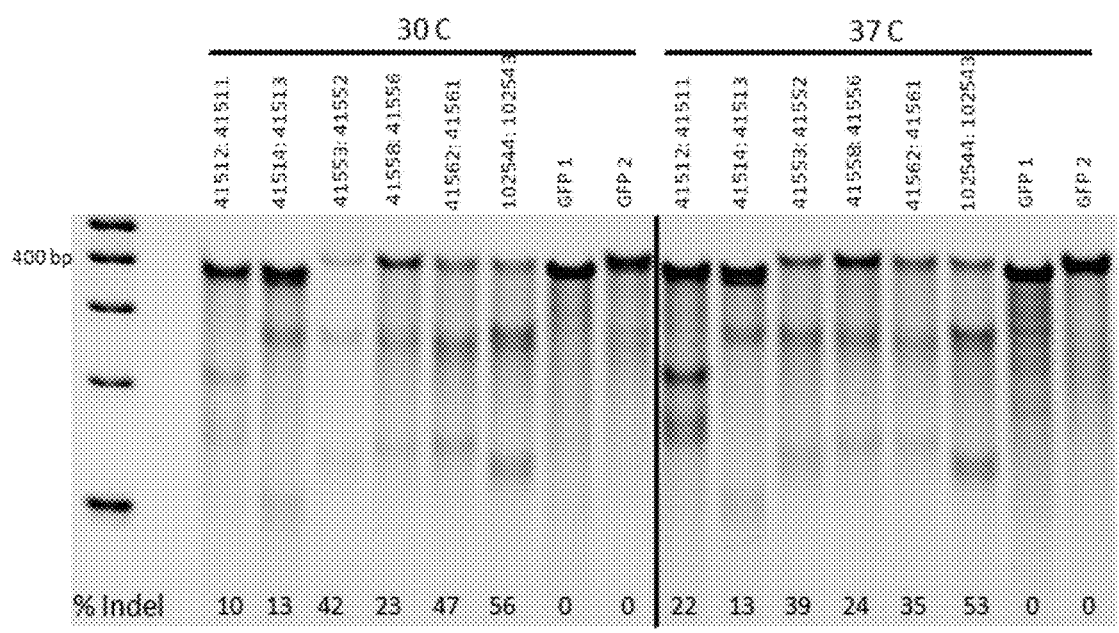
FIG. 2 shows the result of a Surveyor™ nuclease digestion of PCR amplicons of the IL2RG locus after treatment of K562 cells with the indicated ZFNs and TALENs. GFP1 and GFP2 are control lanes where the cells have been transfected with GFP encoding vectors.
Figure 3A:
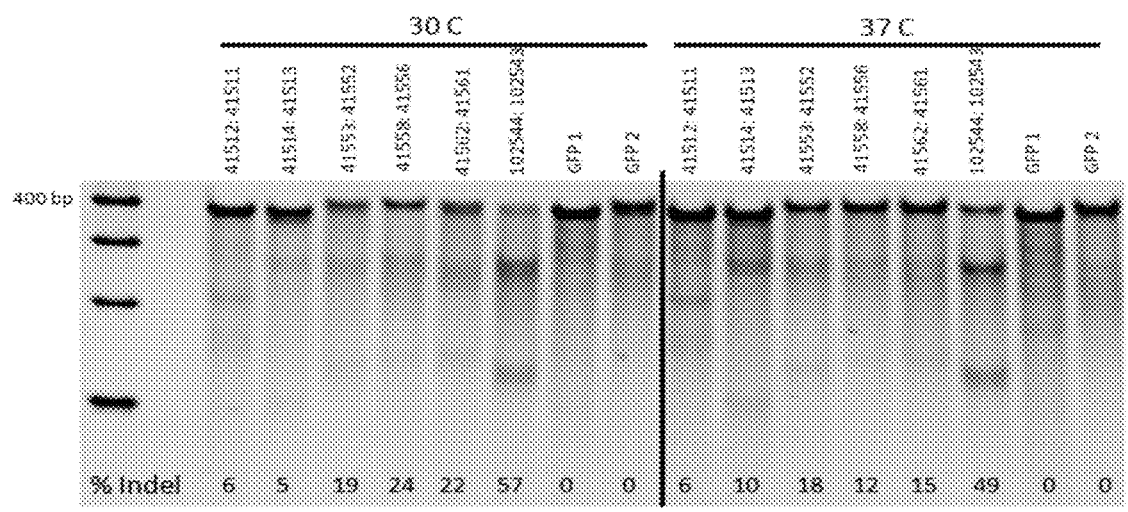

The nucleases cleaved at their respective target sites as expected. Lanes are identified by the nuclease pair or control administered, and the percent of PCR products wherein the nucleotides have been inserted and/or deleted ("indels") are indicated at the bottom of each lane ("% NHEJ"). Exemplary results of gels are shown in FIGS. 2 and 3A. FIG. 3B and Table 6 below show high-throughput DNA sequencing analysis (% indels) of K562 cells containing the indicated exemplary ZFN pairs (top line) at day 3 and day 10 post-ZFN introduction. GFP (bottom line) served as a negative control. As shown, 44298:44271 ZFN pair yielded highest DNA cleaving activity.

TABLE 5

Exemplary guide RNAs

| Gene | Locus | gRNA/PAM Sequence | SEQ ID NO | GRCh38.p2 Primary Assembly Location |
|---|---|---|---|---|
| IL2RG | Intron 1 | CACATGATTGTAATGGCCAGTGG | 85 | 71111326-71111348 |
| IL2RG | Intron 1 | TTCTGCCCACATGATTGTAATGG | 86 | 71111319-71111341 |
| IL2RG | Intron 1 | CACTGGCCATTACAATCATGTGG | 87 | 71111347-71111325 |
| RAG1 | Intron 2 | TTGAGCACACAGTTATTACTTGG | 88 | 36569004-36569026 |
| RAG1 | Intron 2 | TCTTCCAAATGGGTCATAAAAGG | 89 | 36572801-36572779 |
| RAG1 | Intron 1 | CTGCGCTCAAGGCTGGAGCTTGG | 90 | 36565503-36565525 |
| RAG1 | Intron 1 | CCCAGACTAGTGATTAGCTGTGG | 91 | 36565498-36565476 |
| RAG2 | Intron 2 | TCCCAGCTCCTTGGATGGAATGG | 92 | 36594389-36594367 |
| RAG2 | Intron 2 | AACCGCTACCCTGGTATTGCTGG | 93 | 36594713-36594735 |
| RAG2 | Intron 1 | TAATTCTGTAGTAAGTAAGCAGG | 94 | 36595263-36595285 |
| RAG2 | Intron 1 | AATATACAACTGAGGGAGACAGG | 95 | 36596442-36596420 |

TABLE 6

ZFN activity

| Sample | Day 3 % Indels | Day 10 % Indels | Sample | Day 3 % Indels | Day 10 % Indels | Sample | Day 3 % Indels | Day 10 % Indels |
|---|---|---|---|---|---|---|---|---|
| 44298:44271 | 42.8 | 36.6 | 44330:44308 | 21.5 | 14.9 | 44364:44357 | 43.6 | 40.0 |
| Site3-Matrix-Day10-2 | 39.9 | 34.7 | Site4-Matrix-Day10-9 | 21.2 | 14.2 | Site5-Matrix-Day10-2 | 40.1 | 37.0 |
| Site3-Matrix-Day10-3 | | 31.6 | Site4-Matrix-Day10-13 | 19.5 | 13.1 | Site5-Matrix-Day10-6 | 40.8 | 36.9 |
| Site3-Matrix-Day10-13 | 34.8 | 28.4 | Site4-Matrix-Day10-4 | 19.5 | 13.0 | Site5-Matrix-Day10-7 | 38.6 | 36.7 |
| Site3-Matrix-Day10-6 | 32.5 | 28.1 | Site4-Matrix-Day10-16 | 21.9 | 12.9 | Site5-Matrix-Day10-13 | 37.7 | 31.1 |
| Site3-Matrix-Day10-11 | 34.8 | 26.9 | Site4-Matrix-Day10-8 | 20.0 | 12.6 | Site5-Matrix-Day10-1 | 35.9 | 31.0 |
| Site3-Matrix-Day10-16 | 36.1 | 26.8 | Site4-Matrix-Day10-12 | 18.1 | 12.6 | Site5-Matrix-Day10-8 | 34.5 | 30.3 |
| Site3-Matrix-Day10-1 | 26.8 | 25.3 | Site4-Matrix-Day10-7 | 19.0 | 12.0 | Site5-Matrix-Day10-14 | 35.2 | 29.2 |
| Site3-Matrix-Day10-9 | 30.6 | 24.8 | Site4-Matrix-Day10-11 | 18.1 | 11.5 | Site5-Matrix-Day10-15 | 36.2 | 29.1 |
| Site3-Matrix-Day10-4 | 27.8 | 24.6 | Site4-Matrix-Day10-1 | 19.9 | 11.4 | Site5-Matrix-Day10-10 | 32.4 | 28.2 |
| Site3-Matrix-Day10-5 | 31.2 | 24.6 | Site4-Matrix-Day10-3 | 18.1 | 11.1 | Site5-Matrix-Day10-9 | 33.3 | 28.1 |
| Site3-Matrix-Day10-15 | 32.5 | 24.3 | Site4-Matrix-Day10-2 | 18.6 | 10.6 | Site5-Matrix-Day10-4 | 29.1 | 27.2 |
| Site3-Matrix-Day10-10 | 26.8 | 24.2 | Site4-Matrix-Day10-15 | 18.4 | 10.3 | Site5-Matrix-Day10-3 | 31.5 | 27.0 |
| Site3-Matrix-Day10-7 | 29.4 | 21.5 | Site4-Matrix-Day10-10 | 17.2 | 9.7 | Site5-Matrix-Day10-11 | 31.2 | 26.9 |
| Site 3 Parental | 25.1 | 19.6 | Site4-Matrix-Day10-14 | 16.5 | 8.5 | Site5-Matrix-Day10-12 | 28.1 | 25.5 |
| Site3-Matrix-Day10-12 | 22.3 | 16.7 | Site 4 Parental | 14.7 | 8.3 | Site5-Matrix-Day10-16 | 29.5 | 23.8 |
| Site3-Matrix-Day10-8 | 22.3 | 15.1 | Site4-Matrix-Day10-6 | 13.0 | 8.2 | Site 5 Parental | 14.9 | 10.6 |
| GFP | 0.2 | 0.1 | GFP | 0.2 | 0.1 | GFP | 0.2 | 0.1 |

Thus, the nucleases targeted to exon 1 and intron 1 of IL2RG were all capable of cleaving the target gene.

Example 3: Methylcellulose Assay on Nuclease-Modified CD34+ Cells

Differentiation of the CD34+ cells as treated in Example 2 was analyzed by assay of colony types arising from Methocult-induced differentiation: colony-forming units, erythroid ("CFU-E"); burst-forming units, erythroid ("BFU-E"); colony-forming units, granulocyte/macrophage ("CFU-GM") and colony-forming units; granulocyte/erythrocyte/monocyte/macrophage ("CFU-GEMM") using standard methodology as previously described (Genovese et al. (2014) Nature; 510(7504):235-40). In short, CD34+ cells were genome modified, allowed to recover in vitro, then plated in methylcellulose medium and allowed to differentiate for 2 weeks before colonies were analyzed.

Figure 4A:
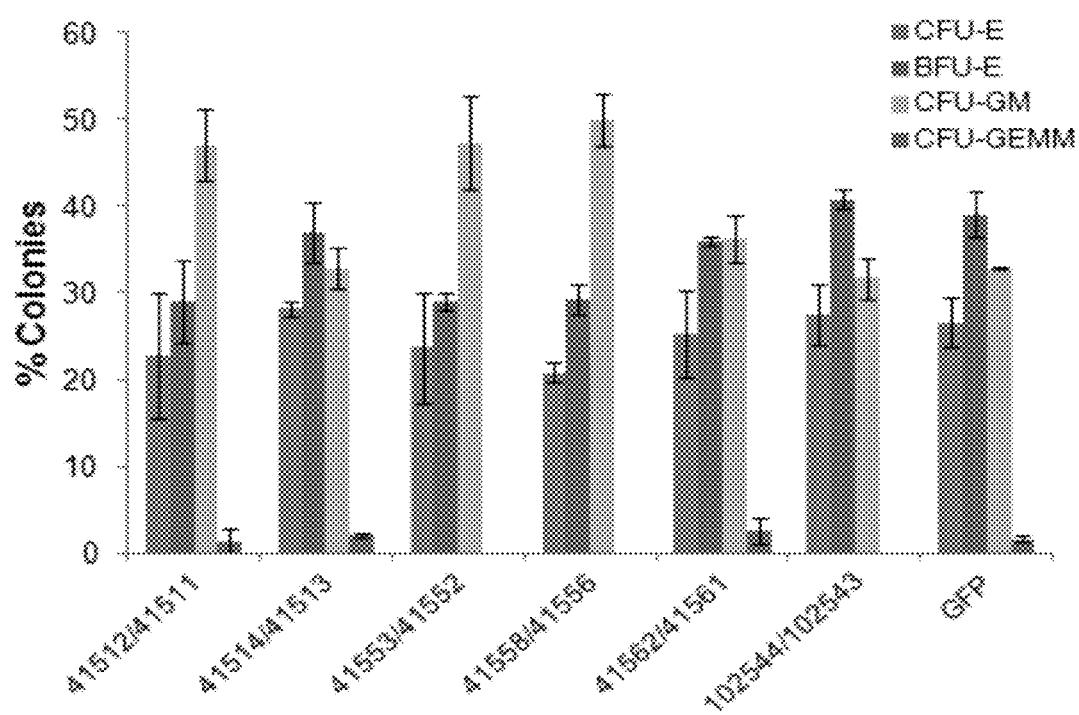
FIGS. 4A and 4B are graphs depicting results of methylcellulose assays on CD34+ cells nucleofected with the nucleases.
Figure 4B:
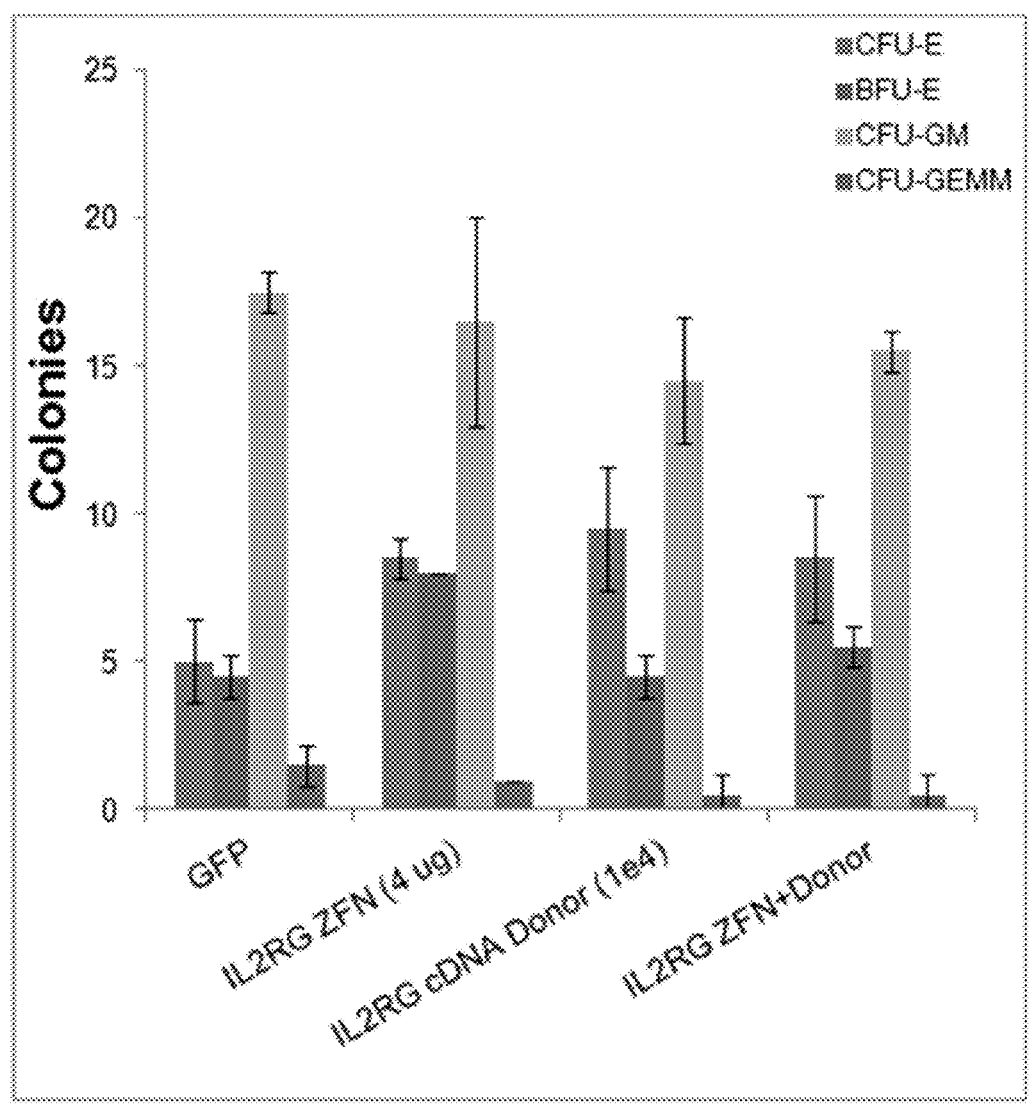

As shown in FIGS. 4A and 4B, the number of colonies formed from differentiated CD34+ HSPCs was not significantly different between groups, however more granulocyte and monocyte forming units were observed in cell pools treated with 3 of the 6 nucleases compared to the GFP control.

Example 4: Targeted IL2RG Donor Insertion

A. Targeted Integration into IL2RG-Inactivated Jurkat Cell Lines

Figure 5D:
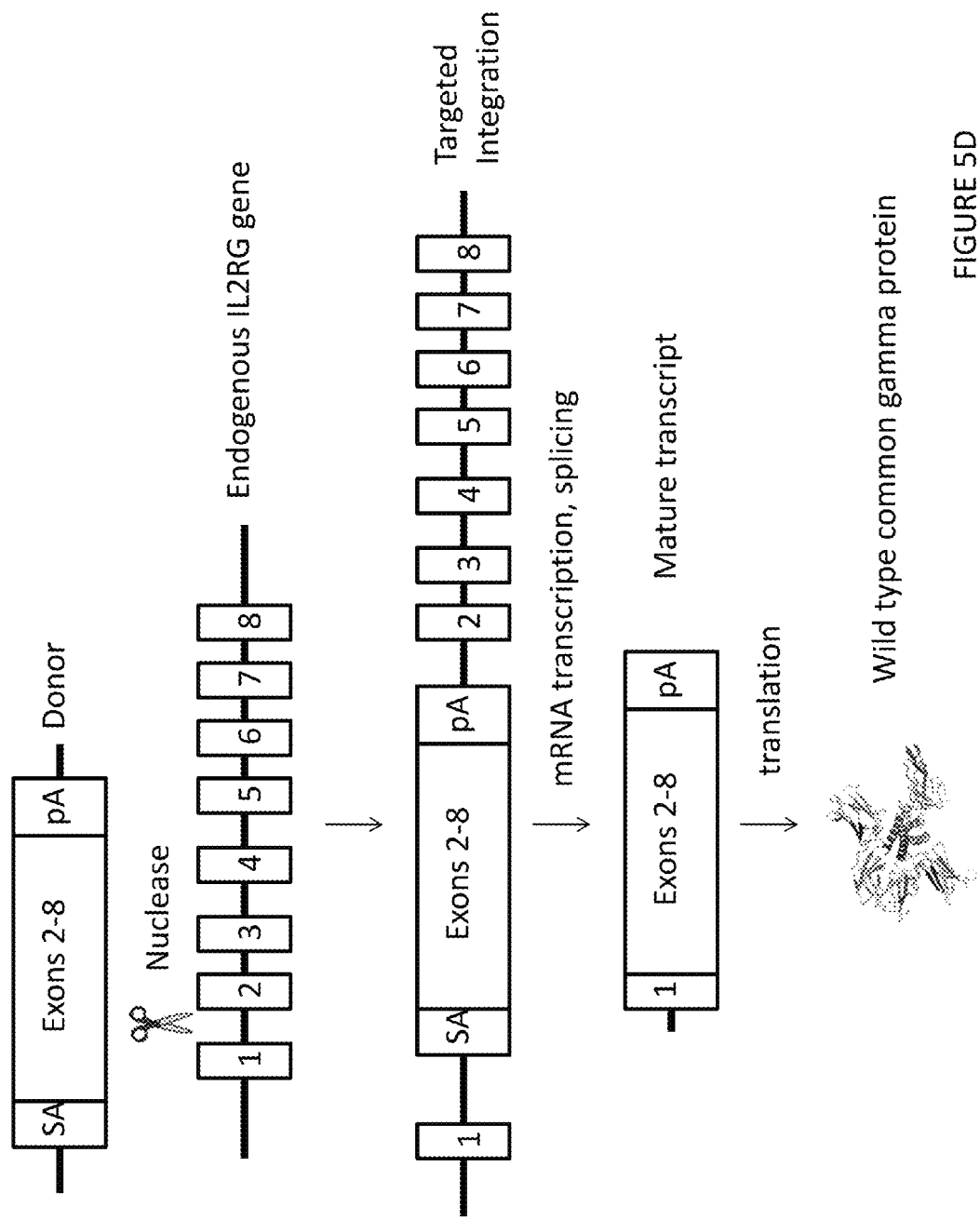

Targeted integration into the IL2RG locus was also performed. Exemplary donor constructs for intron 1 of IL2RG (nucleases described in Example 1) are shown in FIG. 5. In particular, FIG. 5A shows an IL2RG gene with common mutations found in X-SCID patients. FIG. 5B shows an exemplary corrective partial cDNA donor with homology arms flanking the nuclease cleavage site in intron 1, a 5' splice acceptor, and polyadenylation signal tail to terminate transcription. FIG. 5C shows an analogous intron 1 exemplary donor construct with a 2A-GFP construct to assay targeted integration and expression at the endogenous IL2RG locus via flow cytometry or other fluorescence detection assays. FIG. 5D shows an illustration of insertion of the partial IL2RG donor construct into Intron 1 of the IL2RG gene and subsequent production of a wild-type protein.

Jurkat clonal cell lines in which IL2RG was inactivated using ZFNs targeted to exon 5 of IL2RG (see, U.S. Pat. No. 7,888,121) were also prepared. Two clones were chosen for further experiments in which one had a 17 base pair deletion in IL2RG (referred to as clone 2) and the other had a 1 base pair addition (referred to as clone 8). Both modifications yielded nonsense mutations and produced premature stop codons in the coding sequence.

The nucleases (400 ng plasmid DNA/nuclease) and corrective IL2RG donor constructs (1e6 vg/cell AAV6) as shown in FIG. 5 were introduced into clonal cell lines 2 and 8. In short, the AAV6 donor was introduced to cells in RPMI medium, incubated at 37 C for 16 hours, cells were washed, then the nucleases were electroporated using an Amaxa SF kit. Total RNA was harvested 3 days later. The donor were introduced as AAVs and the nucleases as DNA.

Figure 6A:
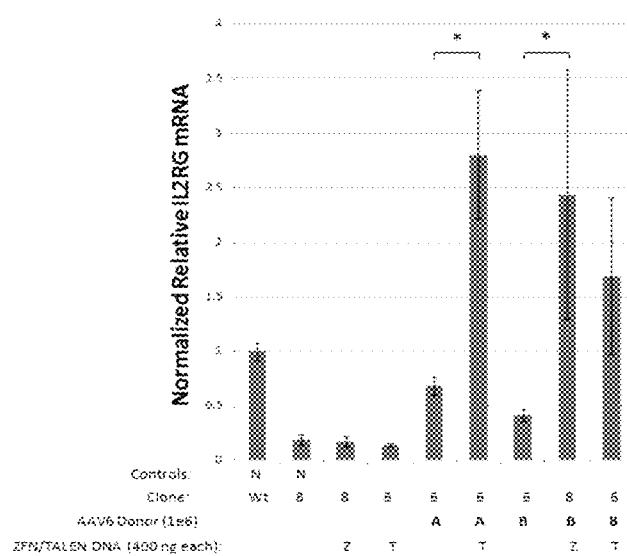
FIGS. 6A and 6B are graphs depicting IL2RG mRNA levels in Jurkat cells treated with the indicated nucleases and/or donors.
Figure 6B:
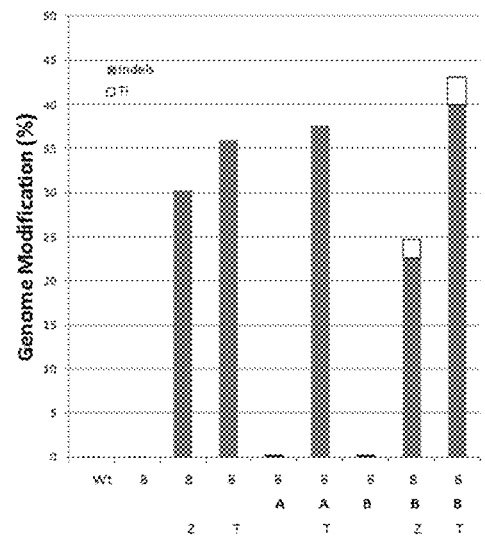
Figure 7A:
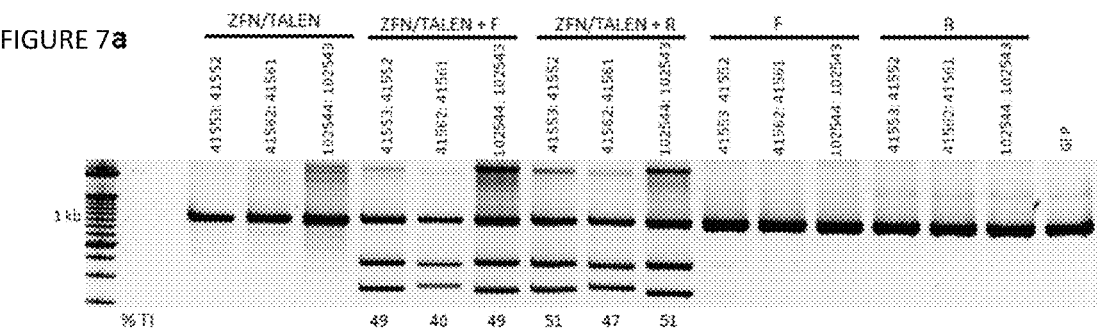
FIGS. 7A and 7B depict detection of targeted integration of a 6 base pair RFLP sequence by restriction enzyme digestion of a PCR amplicon of genomic DNA from K562 cells treated with a 106 base pair single-stranded oligonucleotide donor and the indicated nucleases. "F" indicates use of a forward-strand donor, "R" use of a reverse-strand donor.
Figure 7B:
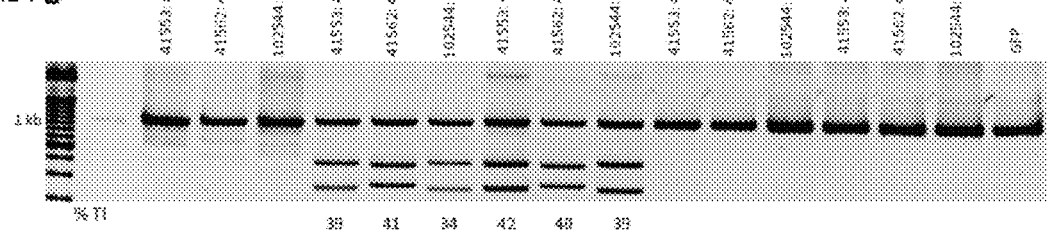
Figure 8A:
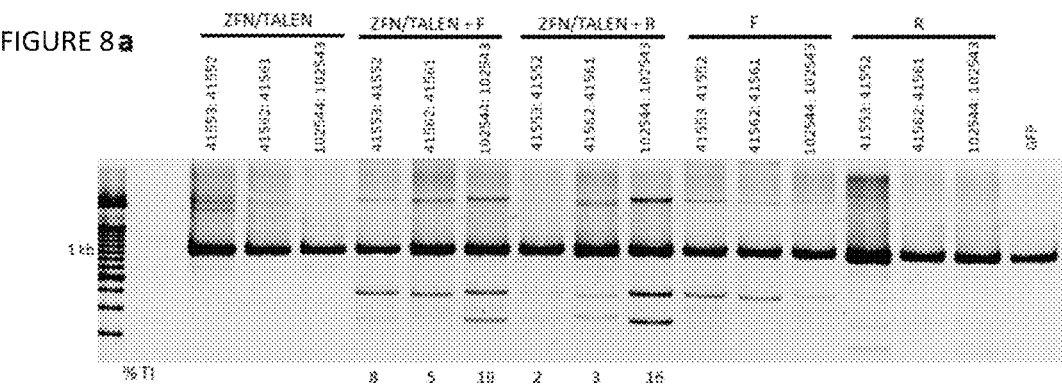
FIGS. 8A and 8B depict detection of targeted integration of a 6 base pair RFLP sequence by restriction enzyme digestion of a PCR amplicon of genomic DNA from CD34+ HSPCs treated with a 106 base pair single-stranded oligonucleotide donor and the indicated nucleases. "F" indicates use of a forward-strand donor, "R" use of a reverse-strand donor.
Figure 8B:
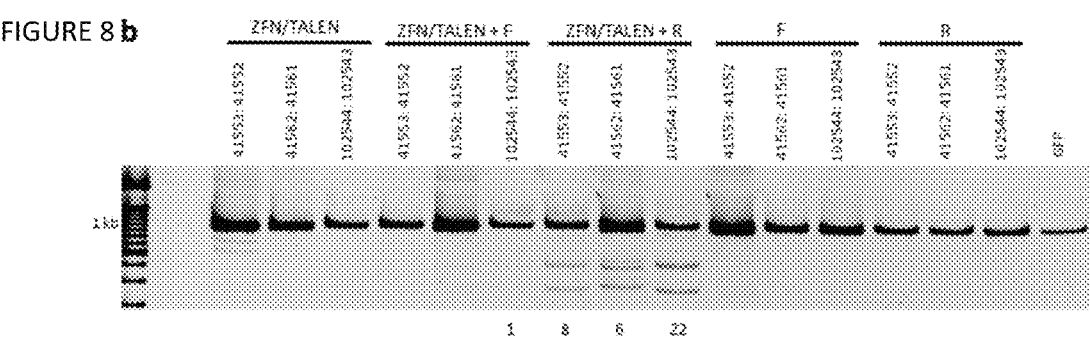
Figure 9A:
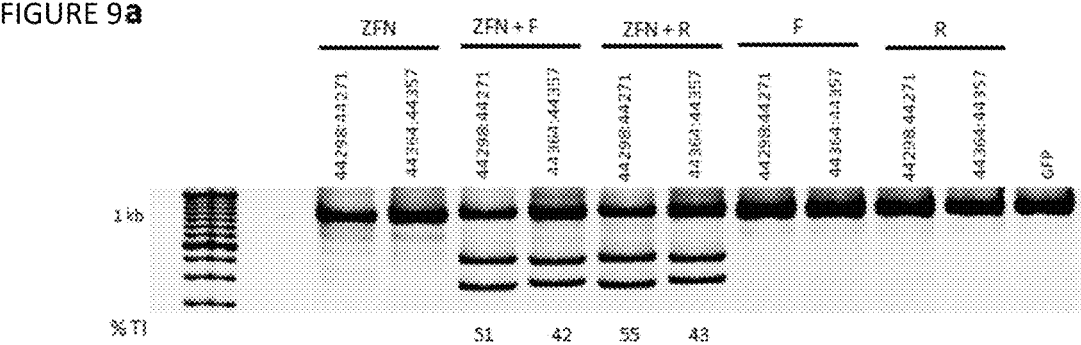
FIGS. 9A and 9B depict detection of targeted integration 3 days post-nucleofection of a 6 base pair RFLP sequence by restriction enzyme digestion of a PCR amplicon of genomic DNA from K562 and CD34+ HSPCs treated with a 106 base pair oligonucleotide donor and the indicated nucleases.
Figure 9B:
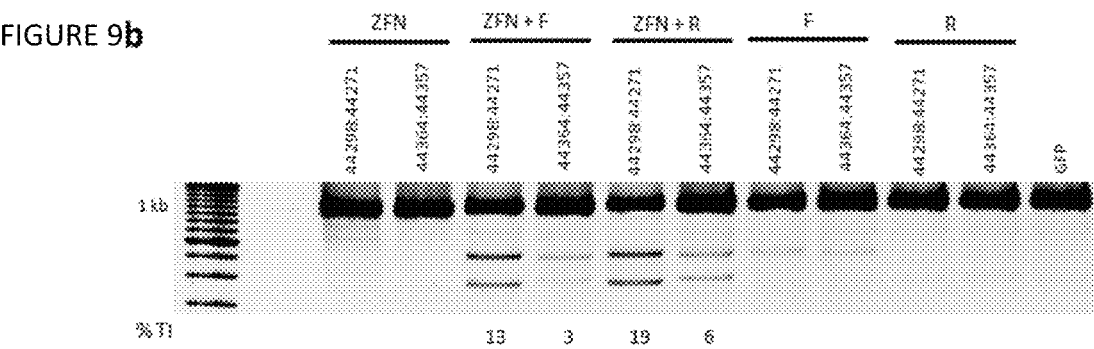
Figure 10A:
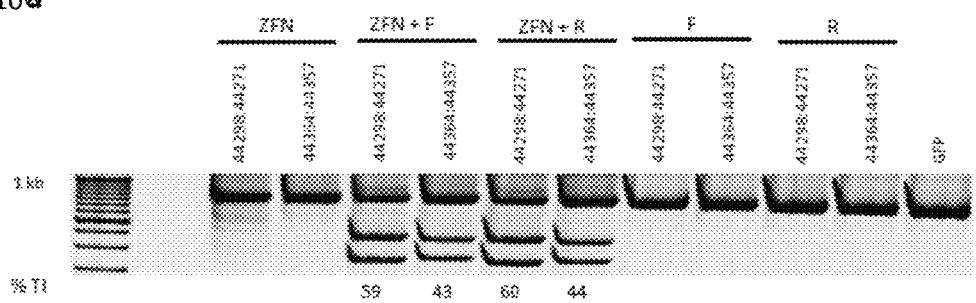
FIGS. 10A and 10B depict detection of targeted integration 10 days post-nucleofection of a 6 base pair RFLP sequence by restriction enzyme digestion of a PCR amplicon of genomic DNA from K562 and CD34+ HSPCs treated with a 106 base pair oligonucleotide donor and with the indicated nucleases.
Figure 10B:
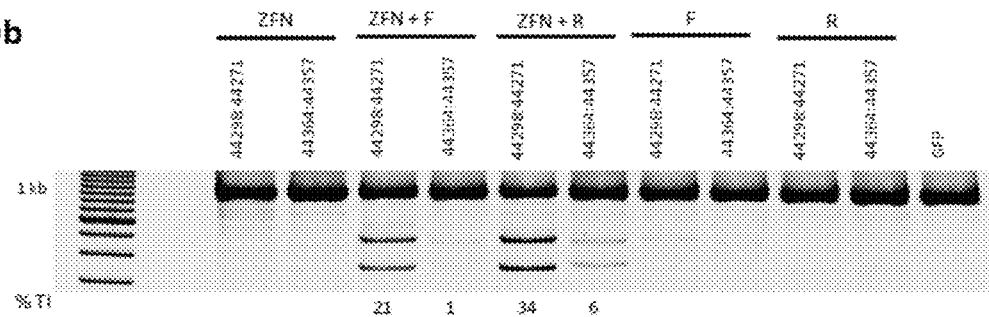

As shown in FIG. 6, IL2RG expression in cell lines with inactivated (exon 5) IL2RG were rescued by nuclease-mediated introduction of a corrective IL2RG transgene using nucleases targeted to intron 1 of IL2RG. Significantly less IL2RG mRNA expression was seen in untreated IL2RG knockouts as compared clones treated with AAV6 partial IL2RG cDNA donor and either TALENs or ZFNs targeting intron 1 of IL2RG. In addition, high-throughput DNA sequencing analysis revealed that less than 5% targeted integration (TI) was sufficient to rescue the total level of IL2RG expression to endogenous levels.

B. Targeted Integration into CD34+ Cells

IL2RG nucleases in the form of mRNA were transfected into peripheral blood mobilized hematopoietic stem cells (CD34+ cells, from a male donor, i.e. these cells only had one copy of the IL2RG gene per cell) or K562 cells. Briefly, 200,000 cells were transfected by BTX nucleofection. The concentrations of nucleases were 40 ug/mL mRNA each per nucleofection. An AAV6 transgene donor (FIG. 5) was delivered 16 hours prior to transfection. Integration of the exogenous DNA sequence into IL2RG was assayed by digestion of a PCR amplicon of the IL2RG locus from treated cells with the MluI restriction enzyme, by PCR using primers outside the donor region of homology, or by high-throughput sequencing (Miseq, Illumina).

As shown in FIGS. 7-10, targeted integration of the 6 bp RFLP sequence was achieved in both CD34+ and K562 cells as determined by digestion with the unique site introduced in the oligo donor.

Figure 11A:
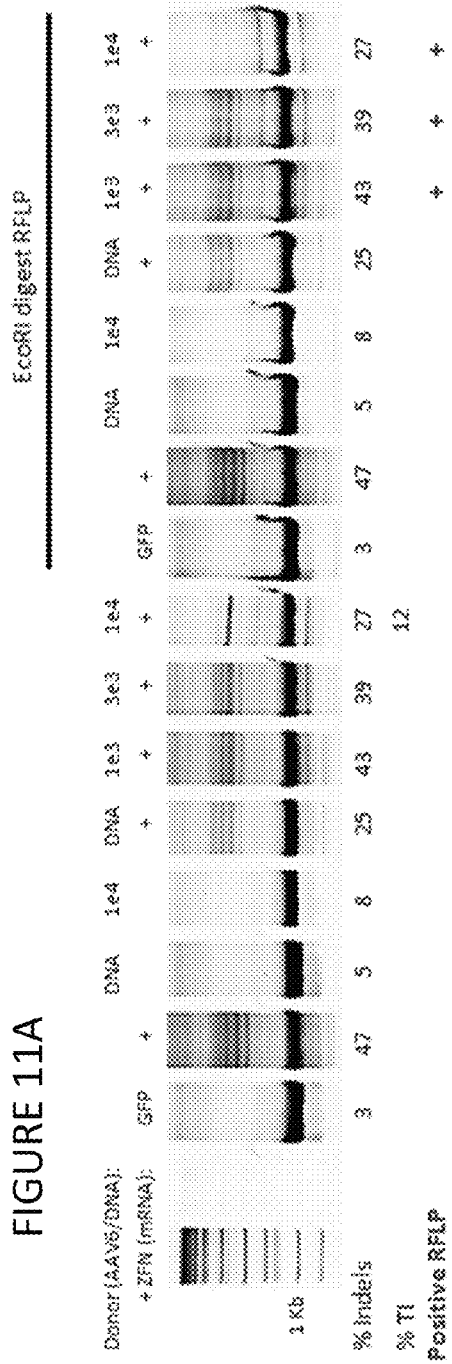
FIGS. 11A and 11B depict targeted integration of an exemplary corrective partial IL2RG cDNA donor in CD34+ cells using the ZFN pair 44271/44298 delivered as mRNA.
Figure 11B:
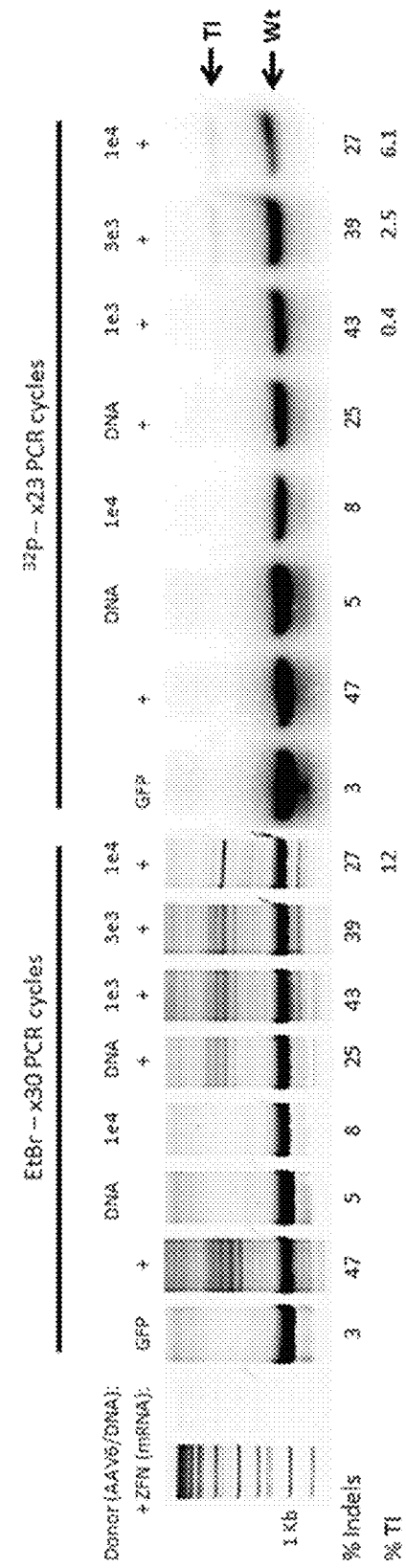
Figure 12:
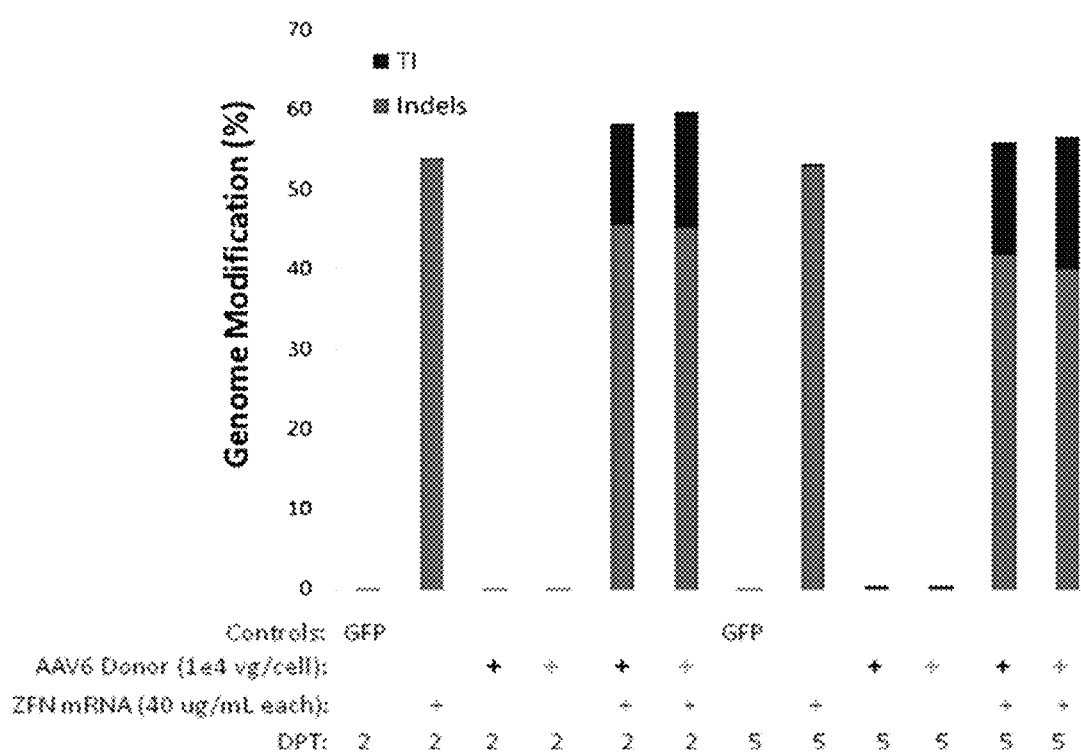
FIG. 12 is a graph depicting targeted integration of corrective partial IL2RG cDNA donor in CD34+ cells analyzed by next generation sequencing. Miseq analysis of NHEJ and TI in CD34 cells yield >50% indels and ~10% TI in cells treated with the ZFN pair 44271/44298 and AAV6 partial IL2RG cDNA donor (grey plus signs), which is stable 2 to 5 days post transfection. Black plus signs indicate SA-2A-GFP donor.
Figure 14A:
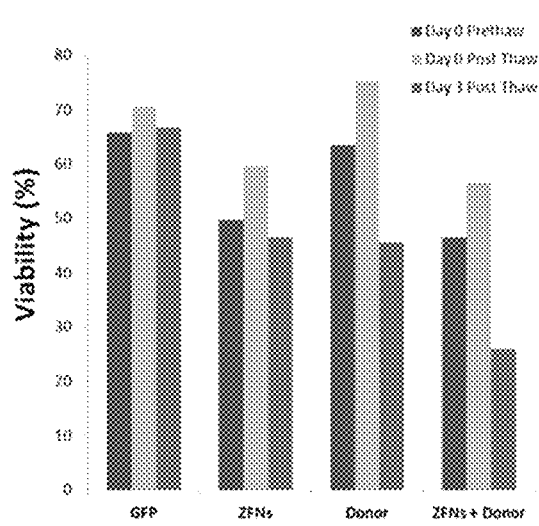
FIGS. 14A and 14B are graphs depicting targeted integration of an exemplary corrective partial IL2RG cDNA donor into CD34+ cells using Maxcyte electroporation, including cryopreserved cells modified with the ZFN pair 44271/44298 delivered as mRNA and a corrective partial IL2RG cDNA donor delivered with AAV6.
Figure 14B:
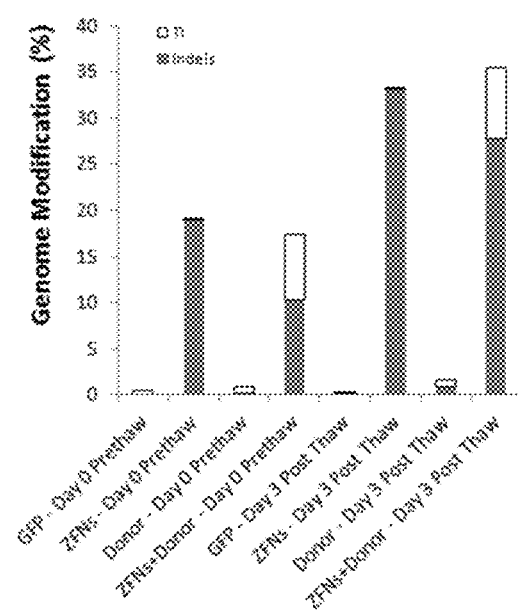

As shown in FIGS. 11 and 12, targeted integration of a corrective partial IL2RG cDNA donor were stably integrated into CD34+ cells as determined by the presence of a donor-specific restriction fragment (FIG. 11) and sequence analysis (FIG. 12). Furthermore, as shown in FIG. 14, cells are viable following TI, cryopreservation and post-thawing of cryopreserved cells.

Genomically edited (via TI) CD34+ cells were also evaluated for differentiation capability as described above in Example 3.

As shown in FIG. 13, no significant differences in lineage differentiation after nuclease or AAV modification was observed. Similarly, no difference in TI in erythroid versus granulocyte/macrophage progenitor clones was observed.

C. Targeted Integration into Safe Harbor Loci

Corrective IL2RG donors may be integrated into safe harbor loci of CD34+ cells, including HPRT, AAVS1, ALB, Rosa26, and/or CCR5 genes using nucleases as described in U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960 to produce functional IL2RG in the cells.

Thus, the results demonstrate that nuclease-mediated stable targeted integration of a corrective IL2RG transgene restored IL2RG expression and that the modified cells maintained their differentiation potential and viability following modification and/or cryopreservation.

Example 5: Targeted Integration into the RAG1 Gene

Figure 15A:
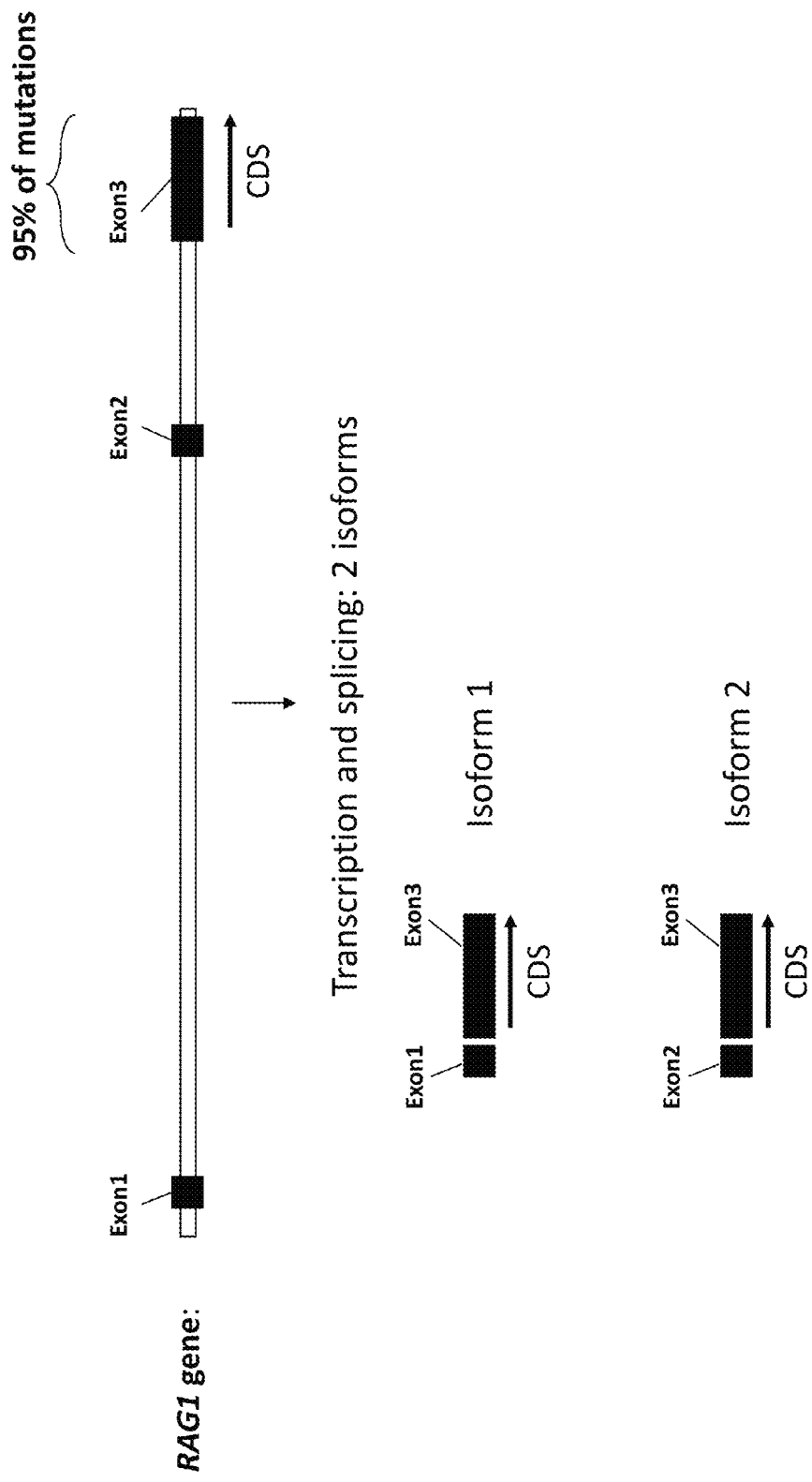
FIGS. 15A and 15B are schematics depicting the RAG genes.
Figure 15B:
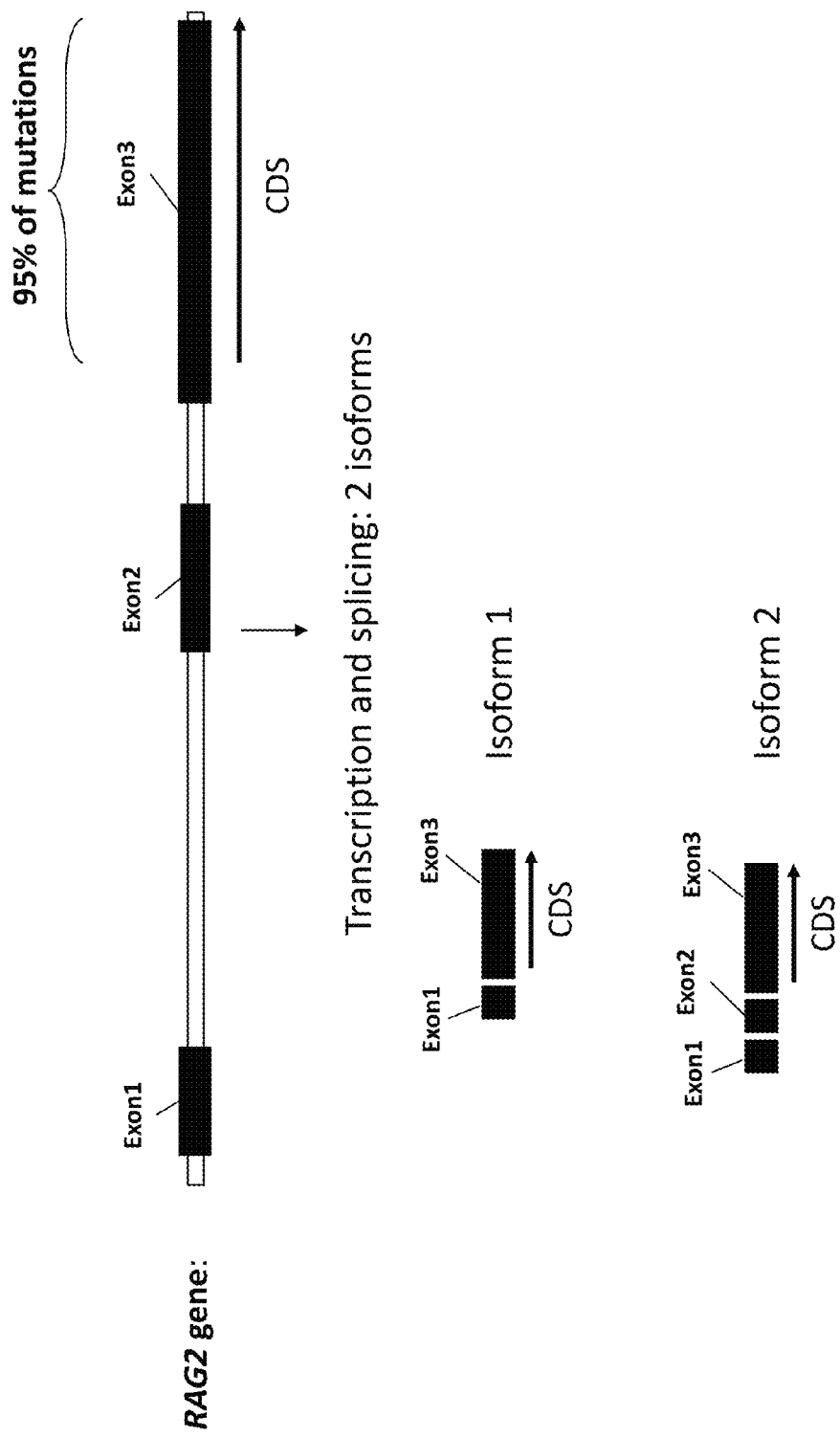

Targeted integration into the RAG1 locus was also performed using exemplary RAG1-targeted ZFNs as shown in Table 1. A schematic of the gene is shown in FIG. 15, demonstrating the two splicing isoforms that arise from this gene. FIG. 16 depicts exemplary donor constructs comprising a corrective cDNA donor with homology arms flanking the nuclease cleavage site in intron 2, a 5' splice acceptor, and polyadenylation signal tail to terminate transcription. Plasmid DNA encoding the ZFN pair 50773/49812, directed to Site 4 in RAG1 intron 2 was introduced into K562 cells with AAV6 comprising the corrective donor.

Figure 17A:
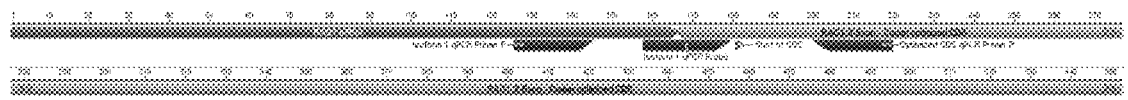
FIG. 17A through 17C are graphs related to assaying functional correction of mature spliced RAG1 transcripts in K562 cells.
Figure 17B:
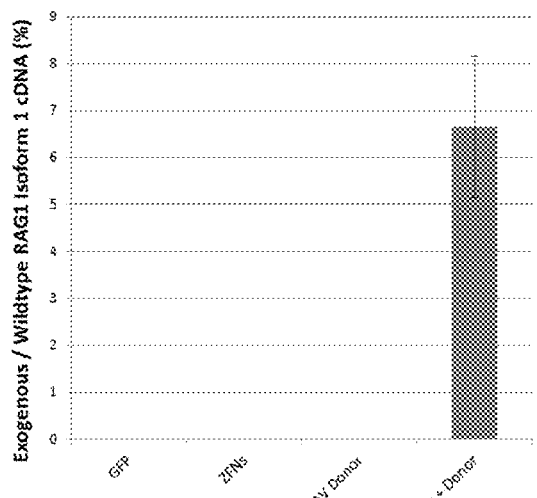
Figure 17C:
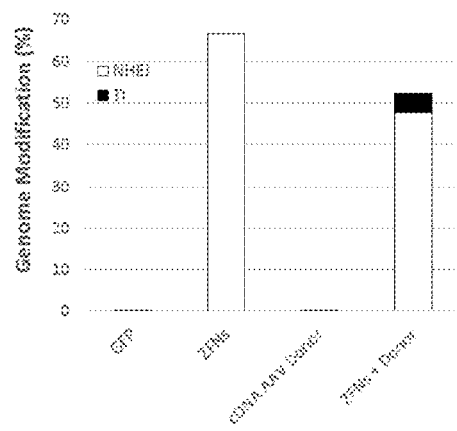

Briefly, human K562 cells were cultured in RPMI supplemented with 10% FBS and 200,000 cells were transfected with 400 ng DNA encoding each of the ZFNs by Amaxa Nucleofector® following the manufacturer's instructions. The cells were also treated with 1e6 vg/cell of the AAV donor. Miseq next-generation sequencing analysis was used to detect ZFN-induced modifications of the target gene (following cleavage). In this assay, PCR-amplification of the target site was followed by deep sequencing on the Illumina platform ("miSEQ") was used according to the manufacturer's instructions to measure editing efficiency as well as nature of editing-generated alleles. The data is shown in FIG. 17, where FIG. 17A depicts a drawing of the location of the primers used for amplifying maturely spliced RAG1 isoform 1 reverse-transcribed cDNA containing the exogenous transgene which had undergone targeted integration into RAG1 intron 2. FIG. 17B shows the relative percentage of exogenous codon-optimized RAG1 cDNA in comparison to wild-type RAG1 isoform 1 cDNA. FIG. 17C shows the amount of genome modification present within these groups and demonstrates the targeted integration of the corrective cDNA in the presence of ZFN and AAV6-donor.

Figure 19A:
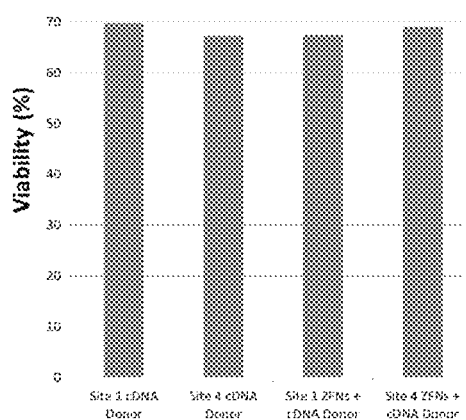
FIGS. 19A and 19B are graphs depicting targeted integration of an exemplary corrective RAG1 cDNA donor into CD34+ cells using Maxcyte electroporation, including cells modified with either the "Site 1" ZFN pair (50698/50718) or the "Site 4" ZFN pair (50773/49812) delivered as mRNA where the corrective RAG1 cDNA donor was delivered with AAV6.
Figure 19B:
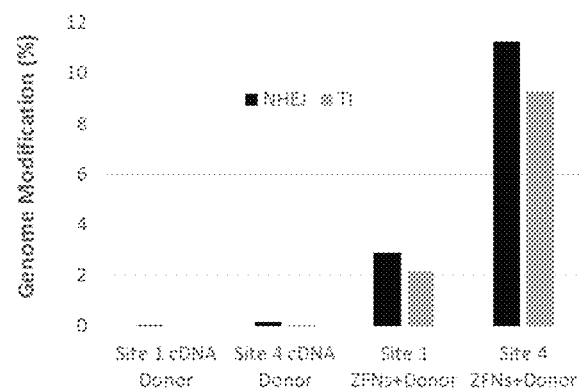

The experiments were performed in CD34+ HSC/PC as well (FIG. 18) and demonstrated that targeted integration of AAV6-delivered cDNA donors occurred using BTX electroporation of RAG1-specific ZFN pairs that targeted both Site 1 (50698/50718) (FIG. 18A) and Site 4 (50773/49812) (FIG. 18B). RAG1-specific ZFNs were also electroporated at large scale into CD34+ HSC/PC (FIG. 19) using the Maxcyte device and were subsequently shown to have targeted integration of AAV6-delivered cDNA donors at both RAG1 intron 2 sites (FIG. 19B). Edited cells were also tested for viability and found to be equally viable in the presence or absence of the ZFNs and AAV6 donor (FIG. 19A).

Ex Vivo Methods

The genetically modified cells, particularly CD34+ HSPCs obtained from X-SCID or Omenn Syndrome subjects (patient-derived CD34+ cells) as previously described (Aiuti et al. (2013) *Science* 341, 1233151), expressing IL2RG or RAG1 as described herein are administered to X-SCID or Omenn Syndrome patients, respectively as previously described (Aiuti et al. ibid).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A host cell comprising an exogenous sequence integrated into intron 1 of an endogenous IL2RG gene or intron 1 or 2 of an endogenous RAG gene using a nuclease comprising a zinc finger protein, a TAL-effector domain or a single guide RNA (sgRNA) DNA-binding domain that binds to a sequence comprising a target site as shown in any of SEQ ID NOs:47-60 or 81-83 or a target site bound by any SEQ ID NO:85-95.

2. The host cell of claim 1, wherein the nuclease comprises the zinc finger protein that comprises recognition helix regions as shown in a single row of Table 1.

3. The host cell of claim 1, wherein the sgRNA comprises a DNA-binding guide RNA as shown in Table 5.

4. The host cell of claim 1, wherein the TALE-effector domain comprises hypervariable diresidues (RVDs) as shown in in a single row of Table 3.

5. The host cell of claim 1, wherein the exogenous sequence is selected from the group consisting of: a sequence encoding an IL2RG polypeptide integrated into intron 1 of an endogenous IL2RG gene; a sequence encoding a RAG polypeptide integrated into intron 1 or 2 of an endogenous RAG gene; and combinations thereof.

6. The host cell of claim 5, wherein the exogenous sequence comprises a cDNA selected from the group consisting of a sequence comprising exons 2 through 8 of a wild type IL2RG gene; a sequence comprising a full-length IL2RG gene; a sequence comprising exon 3 of a wild type RAG gene and a sequence comprising a full-length RAG gene.

7. The host cell of claim 1, wherein the cell is a hematopoietic stem cell or an induced pluripotent stem cell (iPSC).

8. A method of treating or preventing SCID or Omenn Syndrome in a subject, the method comprising administering a host cell according to claim 1 to the subject.

9. The method of claim 8, wherein the cell is a hematopoietic stem cell.

* * * * *